(12) United States Patent
Tomori et al.

(10) Patent No.: US 7,396,930 B2
(45) Date of Patent: Jul. 8, 2008

(54) PROCESS FOR PRODUCING CYCLIC THIOETHER AND SYNTHETIC INTERMEDIATE THEREOF

(75) Inventors: Hiroshi Tomori, Hiratsuka (JP); Keijiro Kobayashi, Hiratsuka (JP); Fumihiko Toriyama, Hiratsuka (JP)

(73) Assignee: Sankyo Company, Limited, Tokyo (JP)

( * ) Notice: Subject to any disclaimer, the term of this patent is extended or adjusted under 35 U.S.C. 154(b) by 560 days.

(21) Appl. No.: 11/006,027

(22) Filed: Dec. 6, 2004

(65) Prior Publication Data

US 2005/0165037 A1    Jul. 28, 2005

Related U.S. Application Data

(63) Continuation of application No. PCT/JP03/07291, filed on Jun. 9, 2003.

(30) Foreign Application Priority Data

Jun. 11, 2002  (JP)  ............................ 2002-169967

(51) Int. Cl.
*C07D 221/20* (2006.01)
*C07D 221/02* (2006.01)

(52) U.S. Cl. .......................................... 546/17; 546/15

(58) Field of Classification Search ................... 546/17, 546/15
See application file for complete search history.

(56) References Cited

U.S. PATENT DOCUMENTS

| 6,159,967 A | 12/2000 | Nishi et al. |
| 6,288,059 B1 | 9/2001 | Nishi et al. |

FOREIGN PATENT DOCUMENTS

| EP | 0 776 893 A1 | 6/1997 |
| JP | 10-182649 A | 7/1998 |
| WO | WO 95/28389 A1 | 10/1995 |
| WO | WO 99/28307 A1 | 6/1999 |
| WO | WO 01/10842 A2 | 2/2001 |
| WO | WO 01/29027 A1 | 4/2001 |
| WO | WO 02/062766 A2 | 8/2002 |

OTHER PUBLICATIONS

Takahide Nishi et al., "Practical Methods for the Preparation of Spiro[benzo[c]thiophene-1(3H),4'-piperidine]-(2S)-Oxide by Resolution and Asymmetric Sulfoxidation", *Tetrahedron: Asymmetry*, vol. 9, (1998), pp. 2567 to 2570.

Hirokazu Kubota et al., "Spiro-Substituted Piperidines as Neurokinin Receptor Antagonists. II.[11] Syntheses and $NK_2$ Receptor-Antagonist Activities of N-[2-Aryl-4-(spiro-substituted piperidin-1'-yl)butyl]carboxamides," *Chem. Pharm. Bull.*, vol. 46, No. 2, (1998), pp. 242 to 254.

William E. Parham et al., "Spira Piperidines, 1. Synthesis of Spiro[isobenzofuran-1(3H),4'-piperidin]-3-ones, Spiro[isobenzofuran-1(3H),4'-piperidines], and Spiro[isobenzotetrahydrothiophene-1(3H),4'-piperidines]," *J. Org. Chem.*, vol. 41, No. 15, (1976), pp. 2628 to 2633.

Takahide Nishi et al., "Combined Tachykinin Receptor Antagonist: Synthesis and Stereochemical Structure-Activity Relationships of Novel Morpholine Analogues," *Bioorg. & Med. Chem. Lett.*, vol. 10, No. 15, (2000), pp. 1665 to 1668.

Takahide Nishi et al., "Combined $NK_1$ and $NK_2$ Tachykinin Receptor Antagonists: Synthesis and Structure-Activity Relationships of Novel Oxazolidine Analogues," *Bioorg. & Med. Chem. Lett.*, vol. 22, No. 9, (1999), pp. 875 to 880.

C.G. Overberger et al., "Preparation of o-Vinylbenzyl d-sec-Butyl Sulfide.[1] An Attempted Asymmetric Polymer Synthesis," *J. Amer. Chem. Soc.*, vol. 78, Feb. 6, 1956, pp. 666 to 669.

Annalisa Tait et al., "Carbamimidothiolic Acid Phenylmethyl Ester Salts and Their N,N'-Tetramethyl Derivatives as Possible Antimicrobial Agents," *Il Farmaco*, vol. 45, No. 6, (1990), pp. 617 to 630.

English-language International Preliminary Examination Report dated Dec. 3, 2003 of International application PCT/JP03/07291 filed Jun. 9, 2003; Applicant: Sankyo Company, Ltd.

*Primary Examiner*—Charanjit S Aulakh
(74) *Attorney, Agent, or Firm*—Frishauf, Holtz, Goodman & Chick, P.C.

(57) ABSTRACT

A process for producing cyclic thioether compounds and their synthetic intermediates. The process produces a compound represented by formula (5):

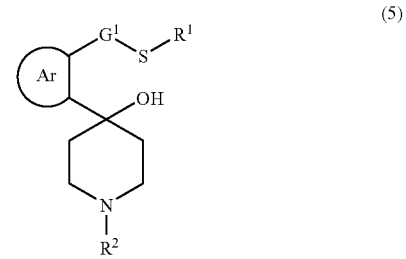

(5)

wherein $G^1$ is an alkylene group, $R^1$ is a thiol protecting group, $R^2$ is hydrogen or an amino protecting group, and Ar is an aryl group or a 5- to 7-membered heteroaryl group.

11 Claims, No Drawings

PROCESS FOR PRODUCING CYCLIC THIOETHER AND SYNTHETIC INTERMEDIATE THEREOF

CROSS-REFERENCE TO RELATED APPLICATION

This application is a continuation application of International application PCT/JP03/07291 filed Jun. 9, 2003, the entire contents of which are incorporated by reference herein.

BACKGROUND OF THE INVENTION

1. Field of the Invention

The present invention relates to a novel process for producing cyclic thioethers, and more particularly, to novel compounds for producing cyclic thioethers, production processes therefor and methods of use.

2. Background Information

The following processes are known as processes for synthesizing cyclic thioethers.

W. E. Parham et al. in J. Org. Chem., 41, 2628 (1976) disclose a process for synthesizing cyclic thioethers by reacting thiourea with 1-bromo-2-(bromomethyl)benzene and hydrolysis thereof to obtain (2-bromophenyl)methanethiol, and then following lithium-halogen exchange of (2-bromophenyl)methanethiol with butyl lithium, reacting the resulting product with a ketone (G represents NMe or CH$_2$) to obtain mercapto alcohol followed finally by a dehydration reaction with sulfuric acid.

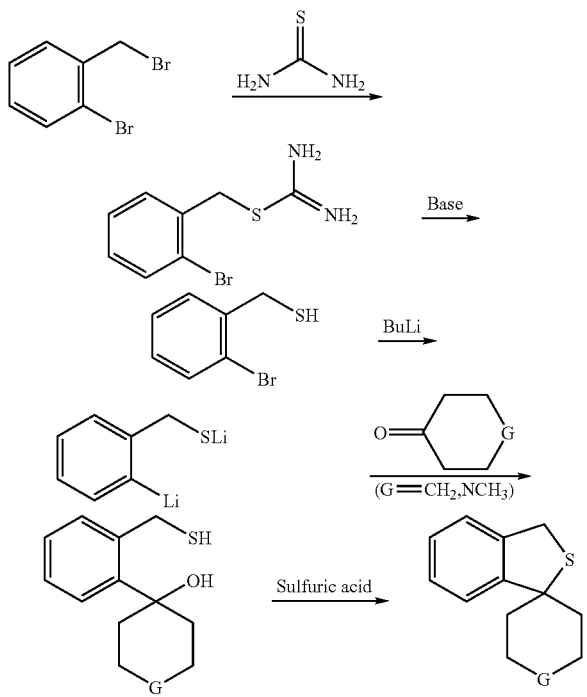

(In the above formula, Bu represents n-butyl, and G represents >CH$_2$ or >NCH$_3$.)

Japanese Patent Application (Kokai) No. Hei 10-182649 discloses a process for synthesizing a cyclic thioether by converting the hydroxyl group of (2-bromophenyl)methanol to a leaving group with a sulfonyl halide such as methanesulfonyl chloride or p-toluenesulfonyl chloride, and after converting to an acetylthio group, removing the acetyl group by hydrolyzing to obtain (2-bromophenyl)methanethiol, and then carrying out a lithium-halogen exchange by reacting with butyl lithium, followed by reacting with a ketone to obtain a mercaptoalcohol compound followed by a dehydration reaction.

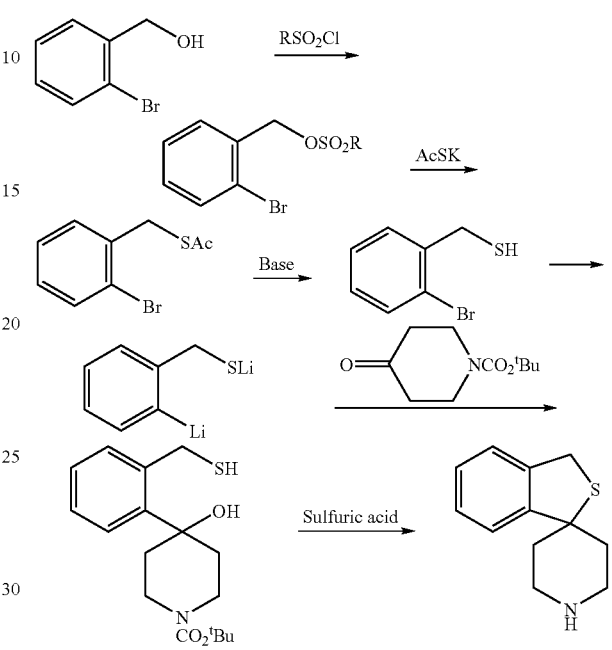

(In the above formula, Ac represents acetyl. Bu represents n-butyl, $^t$Bu represents tert-butyl, and R represents methyl or p-tolyl.)

Hirokazu Kubota et al., Chem. Pharm. Bull., 46, 242 (1998) disclose a process for synthesizing a cyclic thioether by reacting (2-bromophenyl)methanethiol or 2-(2-bromophenyl)ethanethiol with butyl lithium to carry out a lithium-halogen exchange, followed by reaction of the resulting product with a ketone to obtain a mercapto alcohol and finally carrying out a dehydration reaction with trifluoroacetic acid.

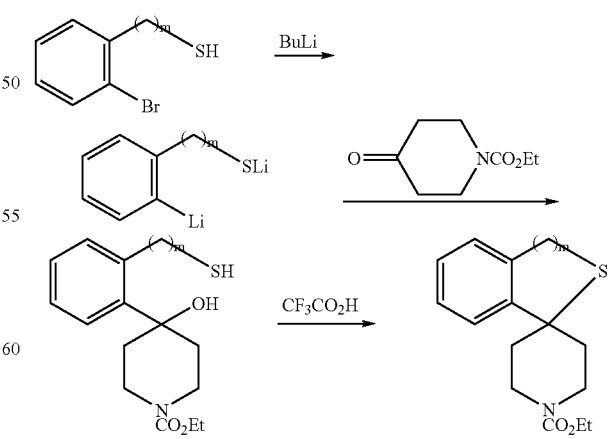

(In the above formula, Bu represents n-butyl, Et represents ethyl, and m represents 1 or 2.)

The (2-bromophenyl)methanethiol used as the starting material in the process of Hirokazu Kubota et al. is known to be synthesized by reacting 1-bromo-2-(bromomethyl)benzene with thiourea or derivatives thereof followed by hydrolysis (Overberger et al., J. Amer. Chem. Soc., 78, 666 (1956) and T. Annalisa et al., Farmaco, 45, 617 (1990)), and the process requires at least two steps.

These processes have the disadvantages of requiring two equivalents of organic lithium reagent (resulting in high costs), having a large number of steps and having a low synthetic yield, and none of the processes are suited for industrial production of cyclic thioethers from the viewpoint of economic feasibility.

As a result of conducting extensive studies for the purpose of overcoming these disadvantages and establishing an industrial process for the production of cyclic thioethers, the inventors of the present invention found that cyclic thioethers can be obtained, by going through the compounds of the general formulae (3) and (5), in fewer steps and less expensively than the known processes, thereby leading to completion of the present invention.

SUMMARY OF THE INVENTION

The present invention relates to (1) a process for producing a compound having the general formula (6):

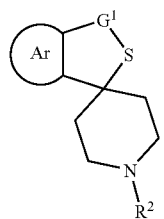

(6)

(wherein $R^2$ represents a hydrogen atom or an amino protecting group, $G^1$ represents a $C_1$-$C_6$ alkylene group and Ar represents a $C_6$-$C_{14}$ aryl group, a $C_6$-$C_{14}$ aryl group substituted with at least one group selected from Substituent group α, a 5- to 7-membered heteroaryl group containing from 1 to 3 sulfur atoms, oxygen atoms and/or nitrogen atoms, or a 5- to 7-membered heteroaryl group containing from 1 to 3 sulfur atoms, oxygen atoms and/or nitrogen atoms and substituted with at least one group selected from Substituent group α, and Substituent group α consists of $C_1$-$C_6$ alkyl groups, $C_1$-$C_6$ alkoxy groups and $C_1$-$C_6$ alkylthio groups) by reacting a compound having the general formula (1):

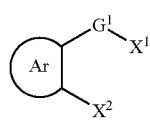

(1)

(wherein $X^1$ and $X^2$ may be the same or different and each represents a halogen atom, and $G^1$ and Ar have the same meanings as defined above) with a compound having the general formula (2):

(2)

(wherein $R^1$ represents a thiol protecting group) to produce a compound represented by the general formula (3):

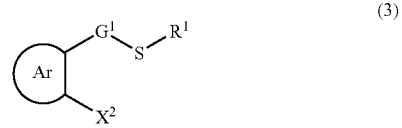

(3)

(wherein $R^1$, $G^1$, $X^2$ and Ar have the same meanings as defined above), and after reacting this with a metal or organometallic reagent that forms a carbanion of this compound, reacting the compound having the general formula (4):

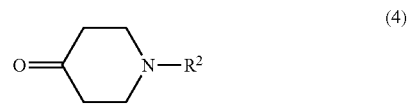

(4)

(wherein $R^2$ has the same meaning as defined above) with the resulting reaction mixture to produce a compound having the general formula (5):

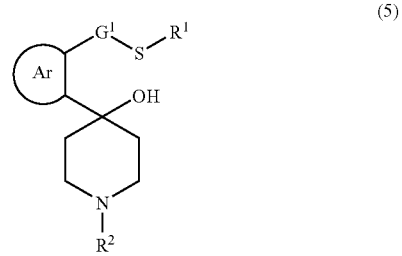

(5)

(wherein $R^1$, $R^2$, $G^1$ and Ar have the same meanings as defined above), carrying out a dehydration reaction after removal of the group $R^1$ from the resulting compound (5), and finally protecting the nitrogen atom if desired with an amino protecting group.

Examples of preferred processes of the above include:

(2) a process wherein Ar represents phenyl, phenyl substituted with at least one group selected from Substituent group α, pyridyl, pyrimidinyl, or pyridyl or pyrimidinyl substituted with at least one group selected from Substituent group α;

(3) a process wherein $G^1$ represents a $C_1$-$C_4$ linear or branched alkylene group;

(4) a process wherein $R^1$ represents a $C_3$-$C_6$ branched alkyl group; an aralkyl group comprising from 1 to 3 $C_6$-$C_{10}$ aryl groups and a $C_1$-$C_3$ alkyl group; or a $C_7$-$C_{15}$ aralkyl group in which the aryl ring is substituted with a $C_1$-$C_4$ alkyl or $C_1$-$C_4$ alkoxy group;

(5) a process wherein $R^2$ represents a hydrogen atom; a $C_1$-$C_4$ alkanoyl group; trifluoroacetyl; methoxyacetyl; benzoyl; 1-naphthoyl; 2-naphthoyl; anisoyl; nitrobenzoyl; a $C_1$-$C_4$ alkoxycarbonyl group; 2,2,2-trichloroethoxycarbonyl; triethylsilylmethoxycarbonyl; 2-(trimethylsilyl)ethoxycarbonyl; vinyloxycarbonyl; allyloxycarbonyl; a $C_1$-$C_6$ linear or branched alkyl group; a $C_3$-$C_6$ linear or branched 2-alkenyl group; an aralkyl group comprising from 1 to 3 $C_6$-$C_{10}$ aryl groups and a $C_1$-$C_3$ alkyl group; benzyloxycarbonyl; or nitrobenzyloxycarbonyl, and, (6) a process wherein $X^1$ and $X^2$ may be the same or different and each represents a chlorine atom or bromine atom.

Moreover, the present invention relates to (7) a compound represented by the general formula (5):

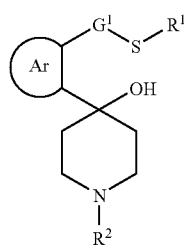

(wherein $G^1$ represents a $C_1$-$C_6$ alkylene group,

R$^1$ represents a thiol protecting group,

R$^2$ represents a hydrogen atom or an amino protecting group,

Ar represents a $C_6$-$C_{14}$ aryl group, a $C_6$-$C_{14}$ aryl group substituted with at least one group selected from the following Substituent group α, a 5- to 7-membered heteroaryl group containing from 1 to 3 sulfur atoms, oxygen atoms and/or nitrogen atoms, or a 5- to 7-membered heteroaryl group containing from 1 to 3 sulfur atoms, oxygen atoms and/or nitrogen atoms and substituted with at least one group selected from Substituent group α, and Substituent group α consists of $C_1$-$C_6$ alkyl groups, $C_1$-$C_6$ alkoxy groups and $C_1$-$C_6$ alkylthio groups).

Preferred examples of the aforementioned compounds include:

(8) a compound wherein R$^1$ represents a $C_3$-$C_6$ branched alkyl group; an aralkyl group comprising from 1 to 3 $C_6$-$C_{10}$ aryl groups and a $C_1$-$C_3$ alkyl group; or a $C_7$-$C_{15}$ aralkyl group in which the aryl ring is substituted with a $C_1$-$C_4$ alkyl or $C_1$-$C_4$ alkoxy group; and, (9) a compound wherein R$^2$ represents a hydrogen atom; a $C_1$-$C_4$ alkanoyl group; trifluoroacetyl; methoxyacetyl; benzoyl; 1-naphthoyl; 2-naphthoyl; anisoyl; nitrobenzoyl; a $C_1$-$C_4$ alkoxycarbonyl group; 2,2,2-trichloroethoxycarbonyl; triethylsilylmethoxycarbonyl; 2-(trimethylsilyl)ethoxycarbonyl; vinyloxycarbonyl; allyloxycarbonyl; a $C_1$-$C_6$ linear or branched alkyl group; a $C_3$-$C_6$ linear or branched 2-alkenyl group; an aralkyl group comprising from 1 to 3 $C_6$-$C_{10}$ aryl groups and a $C_1$-$C_3$ alkyl group; benzyloxycarbonyl; or nitrobenzyloxycarbonyl, while particularly preferred examples of compounds include:

(10) any compound selected from the following compounds:

tert-butyl 4-{2-[(tert-butylthio)methyl]phenyl}-4-hydroxypiperidine-1-carboxylate, ethyl 4-{2-[(tert-butylthio)methyl]phenyl}-4-hydroxypiperidine-1-carboxylate, methyl 4-{2-[(tert-butylthio)methyl]phenyl}-4-hydroxypiperidine-1-carboxylate, benzyl 4-{2-[(tert-butylthio)methyl]phenyl}-4-hydroxypiperidine-1-carboxylate, tert-butyl 4-(2-{[(1,1-dimethylpropyl)thio]methyl}phenyl)-4-hydroxypiperidine-1-carboxylate, ethyl 4-(2-{[(1,1-dimethylpropyl)thio]methyl}phenyl)-4-hydroxypiperidine-1-carboxylate, methyl 4-(2-{[(1,1-dimethylpropyl)thio]methyl}phenyl)-4-hydroxypiperidine-1-carboxylate, benzyl 4-(2-{[(1,1-dimethylpropyl)thio]methyl}phenyl)-4-hydroxypiperidine-1-carboxylate, 1-allyl-4-{2-[(tert-butylthio)methyl]phenyl}piperidin-4-ol, 1-tert-butyl 4-{2-[(tert-butylthio)methyl]phenyl}piperidin-4-ol, 4-{2-[(tert-butylthio)methyl]phenyl}-1-(1,1-dimethylpropyl)piperidin-4-ol, 4-{2-[(tert-butylthio)methyl]phenyl}-1-ethylpiperidin-4-ol, 4-{2-[(tert-butylthio)methyl]phenyl}-1-methylpiperidin-4-ol, 1-benzyl-4-{2-[(tert-butylthio)methyl]phenyl}piperidin-4-ol, 4-{2-[(tert-butylthio)methyl]phenyl}-1-(1-phenylethyl)piperidin-4-ol, 1-allyl-4-(2-{[(1,1-dimethylpropyl)thio]methyl}phenyl)piperidin-4-ol, 1-tert-butyl-4-(2-{[(1,1-dimethylpropyl)thio]methyl}phenyl)piperidin-4-ol, 1-(1,1-dimethylpropyl)-4-(2-{[(1,1-dimethylpropyl)thio]methyl}phenyl)piperidin-4-ol, 4-(2-{[(1,1-dimethylpropyl)thio]methyl}phenyl)-1-ethylpiperidin-4-ol, 4-(2-{[(1,1-dimethylpropyl)thio]methyl}phenyl)-1-methylpiperidin-4-ol, 1-benzyl-4-(2-{[(1,1-dimethylpropyl)thio]methyl}phenyl)piperidin-4-ol, 4-(2-{[(1,1-dimethylpropyl)thio]methyl}phenyl)-1-(1-phenylethyl)piperidin-4-ol, 1-acetyl-4-{2-[(tert-butylthio)methyl]phenyl}piperidin-4-ol, 1-acetyl-4-(2-{[(1,1-dimethylpropyl)thio]methyl}phenyl)piperidin-4-ol, 4-{2-[(tert-butylthio)methyl]phenyl}piperidin-4-ol, and 4-(2-{[(1,1-dimethylpropyl)thio]methyl}phenyl)piperidin-4-ol.

Moreover, the present invention relates to

(11) a process for producing a compound having the general formula (6):

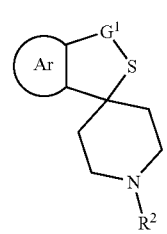

(wherein R$^2$ represents a hydrogen atom or an amino protecting group, $G^1$ represents a $C_1$-$C_6$ alkylene group, and Ar represents a $C_6$-$C_{14}$ aryl group, a $C_6$-$C_{14}$ aryl group substituted with at least one group selected from Substituent group α, a 5- to 7-membered heteroaryl group containing from 1 to 3 sulfur atoms, oxygen atoms and/or nitrogen atoms, or a 5- to 7-membered heteroaryl group containing from 1 to 3 sulfur atoms, oxygen atoms and/or nitrogen atoms and substituted with at least one group selected from Substituent group α, and Substituent group α consists of $C_1$-$C_6$ alkyl groups, $C_1$-$C_6$ alkoxy groups and $C_1$-$C_6$ alkylthio groups) by carrying out a dehydration reaction after removing a group $R^1$ from a compound represented by general formula (5):

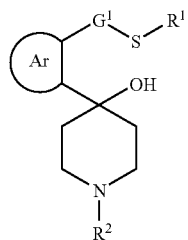

(5)

(wherein $R^1$ represents a thiol protecting group, and $R^2$, $G^1$ and Ar have the same meanings as defined above), and then protecting the nitrogen atom if desired with an amino protecting group).

Examples of preferred processes of the above include:

(12) a process wherein Ar represents phenyl, phenyl substituted with at least one group selected from Substituent group α, pyridyl, pyrimidinyl, or pyridyl or pyrimidinyl substituted with at least one group selected from Substituent group α,

(13) a process wherein $G^1$ represents a $C_1$-$C_4$ linear or branched alkylene group,

(14) a process wherein $R^1$ represents a $C_3$-$C_6$ branched alkyl group; an aralkyl group comprising from 1 to 3 $C_6$-$C_{10}$ aryl groups and a $C_1$-$C_3$ alkyl group; or a $C_7$-$C_{15}$ aralkyl group in which the aryl ring is substituted with a $C_1$-$C_4$ alkyl or $C_1$-$C_4$ alkoxy group, and,

(15) a process wherein $R^2$ represents a hydrogen atom; a $C_1$-$C_4$ alkanoyl group; trifluoroacetyl; methoxyacetyl; benzoyl; 1-naphthoyl; 2-naphthoyl; anisoyl; nitrobenzoyl; a $C_1$-$C_4$ alkoxycarbonyl group; 2,2,2-trichloroethoxycarbonyl; triethylsilylmethoxycarbonyl; 2-(trimethylsilyl)ethoxycarbonyl; vinyloxycarbonyl; allyloxycarbonyl; a $C_1$-$C_6$ linear or branched alkyl group; a $C_3$-$C_6$ linear or branched 2-alkenyl group; an aralkyl group comprising from 1 to $C_6$-$C_{10}$ aryl groups and a $C_1$-$C_3$ alkyl group; benzyloxycarbonyl; or nitrobenzyloxycarbonyl.

Moreover, the present invention relates to

(16) a process for producing a compound having the general formula (5):

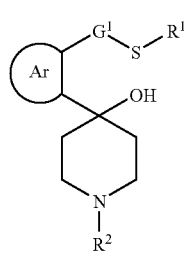

(5)

(wherein $R^1$ represents a thiol protecting group, $R^2$ represents a hydrogen atom or an amino protecting group, $G^1$ represents a $C_1$-$C_6$ alkylene group and Ar represents a $C_6$-$C_{14}$ aryl group, a $C_6$-$C_{14}$ aryl group substituted with at least one group selected from Substituent group α, a 5- to 7-membered heteroaryl group containing from 1 to 3 sulfur atoms, oxygen atoms and/or nitrogen atoms, or a 5- to 7-membered heteroaryl group containing from 1 to 3 sulfur atoms, oxygen atoms and/or nitrogen atoms and substituted with at least one group selected from Substituent group α, and Substituent group α consists of $C_1$-$C_6$ alkyl groups, $C_1$-$C_6$ alkoxy groups and $C_1$-$C_6$ alkylthio groups) by reacting a compound having the general formula (1):

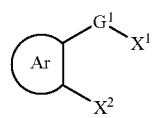

(1)

(wherein $X^1$ and $X^2$ may be the same or different and each represents a halogen atom, and $G^1$ and Ar have the same meanings as defined above) with a compound having the general formula (2):

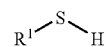

(2)

(wherein $R^1$ has the same meaning as defined above) to produce a compound represented by the general formula (3):

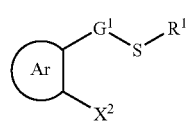

(3)

(wherein $R^1$, $G^1$, $X^2$ and Ar have the same meanings as defined above), and after reacting this with a metal or organometallic reagent that forms a carbanion of this compound, allowing compound (4) having the general formula (4):

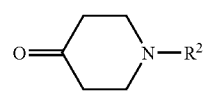

(4)

(wherein $R^2$ has the same meaning as defined above) to act on the resulting reaction mixture.

Examples of preferred processes of the above include:

(17) a process wherein Ar represents phenyl, phenyl substituted with at least one group selected from Substituent group α, pyridyl, pyrimidinyl, or pyridyl or pyrimidinyl substituted with at least one group selected from Substituent group α,

(18) a process wherein $G^1$ represents a $C_1$-$C_4$ linear or branched alkylene group,

(19) a process wherein $R^1$ represents a $C_3$-$C_6$ branched alkyl group; an aralkyl group comprising from 1 to 3 $C_6$-$C_{10}$ aryl groups and a $C_1$-$C_3$ alkyl group; or a $C_7$-$C_{15}$ aralkyl group in which the aryl ring is substituted with a $C_1$-$C_4$ alkyl or $C_1$-$C_4$ alkoxy group,

(20) a process wherein $R^2$ represents a hydrogen atom; a $C_1$-$C_4$ alkanoyl group; trifluoroacetyl; methoxyacetyl; benzoyl; 1-naphthoyl; 2-naphthoyl; anisoyl; nitrobenzoyl; a $C_1$-$C_4$ alkoxycarbonyl group; 2,2,2-trichloroethoxycarbonyl; triethylsilylmethoxycarbonyl; 2-(trimethylsilyl) ethoxycarbonyl; vinyloxycarbonyl; allyloxycarbonyl; a $C_1$-$C_6$ linear or branched alkyl group; $C_3$-$C_6$ linear or branched 2-alkenyl group; an aralkyl group comprising from 1 to 3 $C_6$-$C_{10}$ aryl groups and a $C_1$-$C_3$ alkyl group; benzyloxycarbonyl; or nitrobenzyloxycarbonyl; and,

(21) a process wherein $X^1$ and $X^2$ may be the same or different and each represents a chlorine atom or bromine atom.

Moreover, the present invention relates to

(22) a process substantially consisting of the third step, fourth step and fifth step, described below, for producing a compound or a pharmaceutically acceptable salt thereof having the general formula (9):

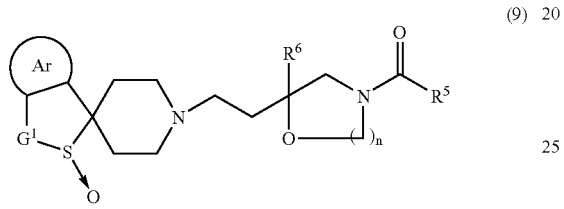
(9)

(wherein Ar represents a $C_6$-$C_{14}$ aryl group, a $C_6$-$C_{14}$ aryl group substituted with at least one group selected from Substituent group α, a 5- to 7-membered heteroaryl group containing from 1 to 3 sulfur atoms, oxygen atoms and/or nitrogen atoms, or a 5- to 7-membered heteroaryl group containing from 1 to 3 sulfur atoms, oxygen atoms and/or nitrogen atoms and substituted with at least one group selected from Substituent group α, $G^1$ represents a $C_1$-$C_6$ alkylene group, $R^5$ represents a phenyl group substituted with from 1 to 3 groups selected from hydroxyl groups, $C_1$-$C_4$ alkoxy groups, $C_1$-$C_4$ halogenated alkyl groups and tetrazolyl groups, $R^6$ represents a phenyl group substituted with 1 or 2 halogen atoms, and n represents 1 or 2); wherein, {the third step is a step wherein a dehydration reaction is carried out after removing a group $R^1$ from a compound represented by the general formula (5):

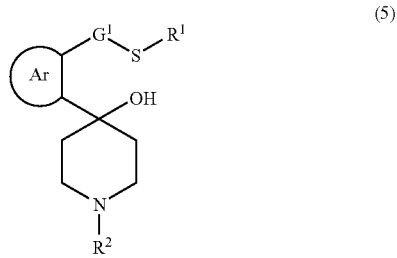
(5)

(wherein $G^1$ and Ar have the same meanings as defined above, $R^1$ represents a thiol protecting group, and $R^2$ represents a hydrogen atom or an amino protecting group), and then the nitrogen atom is protected if desired with an amino protecting group to produce a compound having the general formula (6):

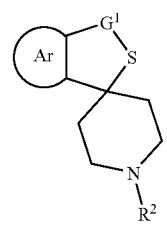
(6)

(wherein $G^1$, $R^2$ and Ar have the same meanings as defined above), the fourth step is a step, wherein the compound of general formula (6) obtained in the third step is oxidized to produce a compound having the general formula (7):

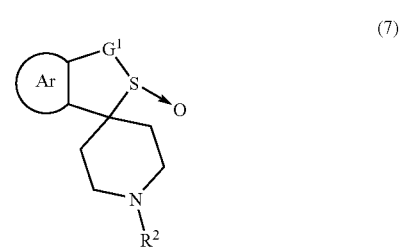
(7)

(wherein $G^1$, $R^2$ and Ar have the same meanings as defined above), and the fifth step is a step, wherein the amino group of the compound of general formula (7) obtained in the fourth step is deprotected if it is protected, followed by reacting with a compound having the general formula (8):

(8)

(wherein n, $R^5$ and $R^6$ have the same meanings as defined above, and Y represents a leaving group) to produce a compound having the aforementioned general formula (9)}.

Examples of preferred processes of the above include:

a process wherein Ar represents phenyl, phenyl substituted with at least one group selected from Substituent group α, pyridyl, pyrimidinyl, or pyridyl or pyrimidinyl substituted with at least one group selected from Substituent group α;

a process wherein $G^1$ represents a $C_1$-$C_4$ linear or branched alkylene group;

a process wherein $R^1$ represents a $C_3$-$C_6$ branched alkyl group; an aralkyl group comprising from 1 to 3 $C_6$-$C_{10}$ aryl groups and a $C_1$-$C_3$ alkyl group; or a $C_7$-$C_{15}$ aralkyl group in which the aryl ring is substituted with a $C_1$-$C_4$ alkyl or $C_1$-$C_4$ alkoxy group, a process wherein $R^2$ represents a hydrogen atom; a $C_1$-$C_4$ alkanoyl group; trifluoroacetyl; methoxyacetyl; benzoyl; 1-naphthoyl; 2-naphthoyl; anisoyl; nitrobenzoyl; a $C_1$-$C_4$ alkoxycarbonyl group; 2,2,2-trichloroethoxycarbonyl; triethylsilylmethoxycarbonyl; 2-(trimethylsilyl)

ethoxycarbonyl; vinyloxycarbonyl; allyloxycarbonyl; a $C_1$-$C_6$ linear or branched alkyl group; a $C_3$-$C_6$ linear or branched 2-alkenyl group; an aralkyl group comprising from 1 to 3 $C_6$-$C_{10}$ aryl groups and a $C_1$-$C_3$ alkyl group; benzyloxycarbonyl; or nitrobenzyloxycarbonyl, a process wherein Y represents a halogen atom, a lower alkanesulfonyloxy group, a halogeno lower alkanesulfonyloxy group or an arylsulfonyloxy group;

a process wherein n is 2:

a process wherein $R^5$ represents 3,5-bis(trifluoromethyl) phenyl, 3,4,5-trimethoxyphenyl, 3-hydroxy-4,5-dimethoxyphenyl, 4-hydroxy-3,5-dimethoxyphenyl or 2-methoxy-5-(1-tetrazolyl)phenyl, and, a process wherein $R^6$ represents a phenyl group substituted with 1 or 2 fluorine atoms or chlorine atoms.

DETAILED DESCRIPTION OF THE INVENTION

The terms or phrases, "$C_6$-$C_{14}$ aryl group", "5- to 7-membered heteroaryl group containing from 1 to 3 sulfur atoms, oxygen atoms and/or nitrogen atoms", "$C_1$-$C_6$ alkylene group", "halogen atom", "$C_1$-$C_6$ alkyl group", "$C_1$-$C_6$ alkoxy group", "$C_1$-$C_6$ alkylthio group", "thiol protecting group", "an amino protecting group", "phenyl group substituted with 1 to 3 groups selected from hydroxy groups, $C_1$-$C_4$ alkoxy groups, $C_1$-$C_4$ halogenated alkyl groups and tetrazolyl groups", "phenyl group substituted with 1 or 2 halogen atoms" and "leaving group", used to specify the present invention are defined below respectively.

The "$C_6$-$C_{14}$ aryl group" and "$C_6$-$C_{14}$ aryl group" portion of the "$C_6$-$C_{14}$ aryl group substituted with at least one group selected from Substituent group α" in the definition of Ar can be, for example, a phenyl, naphthyl, phenanthryl or anthracenyl group, is preferably a phenyl or naphthyl group, and is most preferably a phenyl group.

Furthermore, the aforementioned "$C_6$-$C_{14}$ aryl group" can be condensed with a ring such as a $C_3$-$C_{10}$ cycloalkyl group (and preferably a $C_5$-$C_6$ cycloalkyl group), and an example of such a group is a 5-indanyl group.

The "$C_6$-$C_{14}$ aryl group substituted with at least one group selected from Substituent group α" in the definition of Ar is preferably a $C_6$-$C_{14}$ aryl group substituted with from 1 to 4 groups selected from Substituent group α, is more preferably a $C_6$-$C_{14}$ aryl group substituted with from 1 to 3 groups selected from Substituent group α, and even more preferably a $C_6$-$C_{14}$ aryl group substituted with from 1 to 3 groups selected from methyl, ethyl, methoxy and methylthio.

The "5- to 7-membered heteroaryl group containing from 1 to 3 sulfur atoms, oxygen atoms and/or nitrogen atoms" as well as the "5- to 7-membered heteroaryl group containing from 1 to 3 sulfur atoms, oxygen atoms and/or nitrogen atoms" portion of the "5- to 7-membered heteroaryl group containing from 1 to 3 sulfur atoms, oxygen atoms and/or nitrogen atoms and substituted with at least one group selected from Substituent group α" in the definition of Ar can be, for example, a furyl, thienyl, pyrrolyl, pyrazolyl, imidazolyl, oxazolyl, isoxazolyl, thiazolyl, isothiazolyl, triazolyl, thiadiazolyl, pyridyl, pyridazinyl, pyrimidinyl, pyrazinyl or azepinyl group, is preferably a 5- to 6-membered heteroaryl group containing 1 or 2 sulfur atoms, oxygen atoms and/or nitrogen atoms such as furyl, thienyl, pyrrolyl, pyrazolyl, imidazolyl, oxazolyl, isoxazolyl, thiazolyl, isothiazolyl, pyridyl, pyridazinyl, pyrimidinyl or pyrazinyl group, and more preferably a pyridyl or pyrimidinyl group.

Furthermore, the aforementioned "5- to 7-membered heteroaryl group containing from 1 to 3 sulfur atoms, oxygen atoms and/or nitrogen atoms" can be condensed with another cyclic group (such as a $C_6$-$C_{14}$ aryl group (preferably a $C_6$-$C_{10}$ aryl group) or $C_3$-$C_{10}$ cycloalkyl group (preferably a $C_5$-$C_6$ cycloalkyl group)), and such a group can be an indolyl, benzofuranyl, benzothienyl, quinolyl, isoquinolyl, quinazolinyl, tetrahydroquinolyl or tetrahydroisoquinolyl group.

The "5- to 7-membered heteroaryl group containing from 1 to 3 sulfur atoms, oxygen atoms and/or nitrogen atoms and substituted with at least one group selected from Substituent group α" in the definition of Ar is preferably a 5- to 7-membered heteroaryl group containing from 1 to 3 sulfur atoms, oxygen atoms and/or nitrogen atoms and substituted with 1 to 3 groups selected from Substituent group α, more preferably 5- to 7-membered heteroaryl group containing from 1 to 3 sulfur atoms, oxygen atoms and/or nitrogen atoms and substituted with 1 to 2 groups selected from Substituent group α, and even more preferably a pyridyl group or pyrimidinyl group substituted with 1 to 3 groups selected from methyl, ethyl, methoxy and methylthio.

The "$C_1$-$C_6$ alkylene group" in the definition of $G^1$ can be a linear or branched alkylene group such as a methylene, ethylene, trimethylene, propylene, tetramethylene, 1-methyltrimethylene, 2-methyltrimethylene, 1,1-dimethylethylene, pentamethylene, 1,1-dimethyltrimethylene, 2,2-dimethyltrimethylene, 1,2-dimethyltrimethylene or hexamethylene group, preferably a $C_1$-$C_4$ linear or branched alkylene group, more preferably a $C_1$-$C_3$ linear alkylene group, even more preferably a methylene or ethylene group, and most preferably a methylene group.

The "halogen atom" in the definition of $X^1$ and $X^2$ and the halogen atom of a "phenyl group substituted with 1 or 2 halogen atoms" are fluorine atoms, chlorine atoms, bromine atoms or iodine atoms.

The "$C_1$-$C_6$ alkyl group" in the definition of Substituent group α can be a linear or branched alkyl group such as a methyl, ethyl, propyl, isopropyl, butyl, isobutyl, sec-butyl, tert-butyl, pentyl, isopentyl, 2-methylbutyl, neopentyl, 1-ethylpropyl, hexyl, 4-methylpentyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl or 2-ethylbutyl group, preferably a $C_1$-$C_4$ linear or branched alkyl group, more preferably a methyl, ethyl, propyl, isopropyl or butyl group, and particularly preferably a methyl, ethyl or propyl group.

The "$C_1$-$C_6$ alkoxy group" in the definition of Substituent group α is a group in which an oxygen atom is bonded to the aforementioned "$C_1$-$C_6$ alkyl group", preferably a $C_1$-$C_4$ linear or branched alkoxy group, more preferably a methoxy, ethoxy, propoxy, isopropoxy or butoxy group, and particularly preferably a methoxy, ethoxy or propoxy group.

The "$C_1$-$C_6$ alkylthio group" in the definition of Substituent group α is a group in which a sulfur atom is bonded to the aforementioned "$C_1$-$C_6$ alkyl group", preferably a $C_1$-$C_4$ linear or branched alkylthio group, more preferably a methylthio, ethylthio, propylthio, isopropylthio or butylthio group, and particularly preferably a methylthio, ethylthio or propylthio group.

The "thiol protecting group" in the definition of $R^1$ is a group that is typically used in the field of synthetic organic chemistry as a thiol protecting group, and can be a $C_3$-$C_6$ branched alkyl group such as tert-butyl, 1,1-dimethylpropyl, 1,1,2-trimethylpropyl or 1,1-dimethylbutyl; a $C_3$-$C_6$ linear or branched 2-alkenyl group such as allyl or 1-methyl-2-propenyl; a $C_1$-$C_{22}$ alkanoyl group such as formyl, acetyl, propionyl, butyryl, isobutyryl, pivaloyl, valeryl, isovaleryl, octanoyl, nonanoyl, decanoyl, 3-methylnonanoyl, 8-methylnonanoyl, 3-ethyloctanoyl, 3,7-dimethyloctanoyl, undecanoyl, dodecanoyl, tridecanoyl, tetradecanoyl, pentadecanoyl, hexadecanoyl, 1-methylpentadecanoyl, 14-methylpentadecanoyl, 13,13-dimethyltetradecanoyl, heptadecanoyl, 15-methylhexadecanoyl, octadecanoyl, 1-methylheptadecanoyl, nonadecanoyl, eicosanoyl or heneicosanoyl; a $C_2$-$C_4$ halogenoalkanoyl group such as chloroacetyl, dichloroacetyl, trichloroacetyl or trifluoroacetyl; a $C_1$-$C_4$ alkoxy $C_2$-$C_4$ alkanoyl group such as methoxyacetyl; an unsaturated alkanoyl group such as (E)-2-methyl-2-butenoyl; a $C_6$-$C_{10}$ arylcarbonyl group such as benzoyl, 1-naphthoyl or 2-naphthoyl; a $C_6$-$C_{10}$ halgenoarylcarbonyl group such as a 2-bromobenzoyl or 4-chlorobenzoyl; a $C_1$-$C_4$ alkylated $C_6$-$C_{10}$ arylcarbonyl group such as 2,4,6-trimethylbenzoyl or p-toluoyl; a $C_1$-$C_4$ alkoxylated $C_6$-$C_{10}$ arylcarbonyl group such as a p-anisoyl; a carboxylated $C_6$-$C_{10}$ arylcarbonyl group such as 2-carboxybenzoyl, 3-carboxybenzoyl or 4-carboxybenzoyl; a nitrated $C_6$-$C_{10}$ arylcarbonyl group such as 4-nitrobenzoyl or 2-nitrobenzoyl; a $C_1$-$C_4$ alkoxycarbonylated $C_6$-$C_{10}$ arylcarbonyl group such as 2-(methoxycarbonyl)benzoyl group; a $C_6$-$C_{10}$ arylated $C_6$-$C_{10}$ arylcarbonyl group such as 4-phenylbenzoyl; a tetrahydropyranyl or tetrahydrothiopyranyl group such as tetrahydropyran-2-yl, 3-bromotetrahydropyran-2-yl, 4-methoxytetrahydropyran-4-yl, tetrahydrothiopyran-2-yl or 4-methoxytetrahydrothiopyran-4-yl; a tetrahydrofuranyl or tetrahydrothiofuranyl group such as tetrahydrofuran-2-yl or tetrahydrothiofuran-2-yl; a $C_1$-$C_4$ alkoxymethyl group such as methoxymethyl, ethoxymethyl, propoxymethyl, isopropoxymethyl, butoxymethyl or tert-butoxymethyl; a $C_1$-$C_4$ alkoxylated $C_1$-$C_4$ alkoxymethyl group such as 2-methoxyethoxymethyl; a $C_1$-$C_4$ halogenoalkoxymethyl group such as 2,2,2-trichloroethoxymethyl or bis(2-chloroethoxy)methyl; a $C_1$-$C_4$ alkoxylated ethyl group such as 1-methoxy-1-methylethyl, 1-ethoxyethyl or 1-(isopropoxy)ethyl; an aralkyl group comprising from 1 to 3 $C_6$-$C_{10}$ aryl groups and a $C_1$-$C_3$ alkyl group such as benzyl, 1-naphthylmethyl, 2-naphthylmethyl, diphenylmethyl, triphenylmethyl or 1-naphthyl(diphenyl) methyl; a triarylmethyl group having at least one aryl ring substituted with a $C_1$-$C_4$ alkyl or $C_1$-$C_4$ alkoxy group such as (4-methoxyphenyl)diphenylmethyl, bis(4-methoxyphenyl) phenylmethyl, diphenyl(p-tolyl)methyl or tri(p-tolyl)methyl; a $C_7$-$C_{15}$ aralkyl group in which the aryl ring is substituted with a $C_1$-$C_4$ alkyl group, a $C_1$-$C_4$ alkoxy group, halogen atom, nitro group or cyano group such as 4-methylbenzyl, 2,4,6-trimethylbenzyl, 3,4,5-trimethylbenzyl, 4-methoxybenzyl, 2-nitrobenzyl, 4-nitrobenzyl, 4-chlorobenzyl, 4-bromobenzyl or 4-cyanobenzyl; a $C_1$-$C_4$ alkoxycarbonyl group such as methoxycarbonyl, ethoxycarbonyl, tert-butoxycarbonyl or isobutoxycarbonyl; a $C_1$-$C_4$ halogenated alkoxycarbonyl group such as 2,2,2-trichloroethoxycarbonyl; a $C_2$-$C_5$ alkenyloxycarbonyl group such as vinyloxycarbonyl or allyloxycarbonyl; a $C_7$-$C_{15}$ aralkyloxycarbonyl group in which the aryl ring may or may not be substituted with 1 or 2 $C_1$-$C_4$ alkoxy or nitro groups such as benzyloxycarbonyl, 4-methoxybenzyloxycarbonyl, 3,4-dimethoxybenzyloxycarbonyl, 2-nitrobenzyloxycarbonyl or 4-nitrobenzyloxycarbonyl; or, a silyl group such as trimethylsilyl, triethylsilyl, isopropyldimethylsilyl, tert-butyldimethylsilyl, diisopropylmethylsilyl, di-tert-butylmethylsilyl, triisopropylsilyl, methyldiphenylsiyl, butyldiphenylsilyl, isopropyldiphenylsilyl or diisopropylphenylsilyl, preferably a $C_3$-$C_6$ branched alkyl group; an aralkyl group comprising from 1 to 3 $C_6$-$C_{10}$ aryl groups and a $C_1$-$C_3$ alkyl group, or a $C_7$-$C_{15}$ aralkyl group in which the aryl ring is substituted with a $C_1$-$C_4$ alkyl or $C_1$-$C_4$ alkoxy group, more preferably tert-butyl, 1,1-dimethylpropyl, 1,1,2-trimethylpropyl, benzyl, diphenylmethyl, triphenylmethyl, 4-methylbenzyl or 4-methoxybenzyl, and particularly preferably tert-butyl, 1,1-dimethylpropyl or triphenylmethyl.

The "amino protecting group" in the definition of $R^2$ is a group that is typically used in the field of synthetic organic chemistry as an amino protecting group, and can be a $C_1$-$C_6$ alkanoyl group such as formyl, acetyl, propionyl, butyryl, isobutyryl, pivaloyl, valeryl, isovaleryl or hexanoyl; a $C_1$-$C_4$ alkanoyl group substituted with halogen or $C_1$-$C_4$ alkoxy group such as chloroacetyl, dichloroacetyl, trichloroacetyl, trifluoroacetyl, 3-fluoropropionyl, 4,4-dichlorobutyryl, methoxyacetyl, butoxyacetyl, ethoxypropionyl or propoxybutyryl; an unsaturated $C_2$-$C_4$ alkanoyl group such as acryloyl, propioloyl, methacryloyl, crotonoyl or isocrotonoyl; a $C_6$-$C_{10}$ arylcarbonyl group which may or may not be substituted with halogen, $C_1$-$C_4$ alkyl, $C_1$-$C_4$ alkoxy, $C_1$-$C_4$ alkoxycarbonyl, $C_6$-$C_{10}$ aryl or nitro such as benzoyl, 1-naphthoyl, 2-naphthoyl, 2-fluorobenzoyl, 2-bromobenzoyl, 2,4-dichlorobenzoyl, 6-chloro-1-naphthoyl, p-toluoyl, 4-propylbenzoyl, 4-tert-butylbenzoyl, 2,4,6-trimethylbenzoyl, 6-ethyl-1-naphthoyl, p-anisoyl, 4-propoxybenzoyl, 4-tert-butoxybenzoyl, 6-ethoxy-1-naphthoyl, 2-ethoxycarbonylbenzoyl, 4-tert-butoxycarbonylbenzoyl, 6-methoxycarbonyl-1-naphthoyl, 4-phenylbenzoyl, 4-phenyl-1-naphthoyl, 6-phenyl-1-naphthylbenzoyl, 4-nitrobenzoyl, 2-nitrobenzoyl or 6-nitro-1-naphthoyl; a $C_1$-$C_4$ alkoxycarbonyl group which may or may not be substituted with a halogen or tri-$C_1$-$C_4$ alkylsilyl group such as methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, chloromethoxycarbonyl, 2,2,2-trichloroethoxycarbonyl, 2-fluoropropoxycarbonyl, 2-bromo-1,1-dimethylethoxycarbonyl, 2,2-dibromo-1,1-dimethylethoxycarbonyl, triethylsilylmethoxycarbonyl, 2-(trimethylsilyl) ethoxycarbonyl, 4-(tripropylsilyl)butoxycarbonyl or 3-(tert-butyldimethylsilyl)propoxycarbonyl; a $C_2$-$C_5$ alkenyloxycarbonyl group such as vinyloxycarbonyl, allyloxycarbonyl, 1,3-butadienyloxycarbonyl or 2-pentenyloxycarbonyl; a $C_1$-$C_6$ linear or branched alkyl group such as methyl, ethyl, propyl, isopropyl, butyl, isobutyl, sec-butyl, tert-butyl, 1,1-dimethylbutyl, 1,1-dimethylpropyl or 1,1,2-trimethylpropyl; a $C_3$-$C_6$ linear or branched 2-alkenyl group such as allyl or 1-methyl-2-propenyl; an aralkyl group comprising from 1 to 3 $C_6$-$C_{10}$ aryl groups and a $C_1$-$C_3$ alkyl group such as benzyl, 1-phenylethyl, 2-phenylethyl, 3-phenylpropyl, 4-phenylbutyl, 1-naphthylmethyl, 2-naphthylmethyl, diphenylmethyl, triphenylmethyl or 1-naphthyidiphenylmethyl; a triarylmethyl group having at least one aryl ring substituted with a $C_1$-$C_4$ alkyl or $C_1$-$C_4$ alkoxy group such as (4-methoxyphenyl)diphenylmethyl, bis(4-methoxyphenyl) phenylmethyl; diphenyl(p-tolyl)methyl or tri(p-tolyl)methyl; a $C_7$-$C_{15}$ aralkyl group in which the aryl ring is substituted with from 1 to 3 $C_1$-$C_4$ alkyl, $C_1$-$C_4$ alkoxy, halogen atoms, nitro or cyano groups such as 4-methylbenzyl, 2,4,6-trimethylbenzyl, 3,4,5-trimethylbenzyl, 4-methoxybenzyl, 2,6-dimethoxybenzyl, 2-nitrobenzyl, 4-nitrobenzyl, 4-chlorobenzyl, 2,6-dichlorobenzyl, 4-bromobenzyl or 4-cyanobenzyl; a $C_7$-$C_{15}$ aralkyloxycarbonyl group which may or may not be substituted with methoxy or nitro such as benzyloxycarbonyl, (1-phenyl)benzyloxycarbonyl, 1-naphthyloxycarbonyl, 2-naphthylmethyloxycarbonyl, 9-anthrylmethyloxycarbonyl, 4-methoxybenzyloxycarbonyl or 4-nitrobenzyloxycarbonyl; a lower alkanesulfonyl group such as methanesulfonyl or ethanesulfonyl; a halogeno lower alkanesulfonyl group such as trifluoromethanesulfonyl or pentafluoroethanesulfonyl; or an arylsulfonyl group such as benzenesulfonyl, p-toluenesulfonyl or 4-nitrobenzenesulfonyl, preferably a $C_1$-$C_4$ alkanoyl group; trifluoroacetyl; methoxyacetyl; benzoyl; 1-naphthoyl; 2-naphthoyl; anisoyl; nitrobenzoyl; a $C_1$-$C_4$ alkoxycarbonyl group; 2,2,2-trichloroethoxycarbonyl; triethylsilylmethoxycarbonyl; 2-(trimethylsilyl) ethoxycarbonyl; vinyloxycarbonyl; allyloxycarbonyl; a $C_1$-$C_6$ linear or branched alkyl group; a $C_3$-$C_6$ linear or branched 2-alkenyl group; an aralkyl group comprised of from 1 to 3 $C_6$-$C_{10}$ aryl and $C_1$-$C_3$ alkyl group; benzyloxycarbonyl; 4-nitrobenzyloxycarbonyl; or an arylsulfonyl group; more preferably formyl, acetyl, benzoyl, p-anisoyl, 4-nitrobenzoyl, methoxycarbonyl, ethoxycarbonyl, butoxycarbonyl, tert-butoxycarbonyl, methyl, ethyl, tert-butyl, 1,1-dimethylbutyl, 1,1-dimethylpropyl, 1,1,2-trimethylpropyl, allyl, 1-methyl-2-propenyl, benzyl, 1-phenylethyl, benzyloxycarbonyl or 4-nitrobenzyloxycarbonyl; and particularly preferably methoxycarbonyl, ethoxycarbonyl, tert-butoxycarbonyl, tert-butyl, 1,1-dimethylbutyl, 1,1-dimethylpropyl or 1-phenylethyl.

The $C_1$-$C_4$ alkoxy group of the "phenyl group substituted with from 1 to 3 groups selected from hydroxyl groups, $C_1$-$C_4$ alkoxy groups, $C_1$-$C_4$ halogenated alkyl groups and tetrazolyl" in the definition of $R^5$ can be a linear or branched alkoxy group such as methoxy, ethoxy, propoxy, isopropoxy or butoxy, preferably methoxy, ethoxy or propoxy, more preferably methoxy or ethoxy; and particularly preferably methoxy.

The $C_1$-$C_4$ halogenated alkyl group of the "phenyl group substituted with from 1 to 3 groups selected from hydroxyl groups, $C_1$-$C_4$ alkoxy groups. $C_1$-$C_4$ halogenated alkyl groups and tetrazolyl" in the definition of $R^5$ is a group in which one or two or more of the hydrogen atoms of the $C_1$-$C_4$ alkyl group is replaced with the aforementioned "halogen atom", preferably trifluoromethyl, trichloromethyl, difluoromethyl, dichloromethyl, dibromomethyl, fluoromethyl, 2,2,2-trichloroethyl, 2,2,2-trifluoroethyl, 2-bromoethyl, 2-chloroethyl, 2-fluoroethyl or 2,2-dibromoethyl, more preferably trifluoromethyl, trichloromethyl, difluoromethyl or fluoromethyl, and particularly preferably trifluoromethyl.

Although there are no particular limitations on the "leaving group" in the definition of Y, provided that it is a leaving group that is used during nucleophilic substitution reactions, it can be, for example, a halogen atom such as chlorine, bromine or iodine; a lower alkoxycarbonyloxy group such as methoxycarbonyloxy or ethoxycarbonyloxy; a lower alkanesulfonyloxy group such as methanesulfonyloxy or ethanesulfonyloxy; a halogeno lower alkanesulfonyloxy group such as trifluoromethanesulfonyloxy or pentafluoroethanesulfonyloxy; or an arylsulfonyloxy group such as benzenesulfonyloxy, p-toluenesulfonyloxy or 4-nitrobenzenesulfonyloxy, more preferably a halogen atom, halogeno lower alkanesulfonyloxy group or arylsulfonyloxy group, and even more preferably an arylsulfonyloxy group.

Although the abbreviations used in general formulae (1), (2), (3), (4), (5), (6), (7), (8) and (9), namely Ar, $G^1$, $R^1$, $R^2$, $R^5$, $R^6$, $X^1$, $X^2$ and n are as defined above respectively, examples of preferred groups are indicated below.

Ar is preferably phenyl, phenyl substituted with at least one group selected from Substituent group α, pyridyl, pyrimidinyl, or pyridyl or pyrimidinyl substituted with at least one group selected from Substituent group α, more preferably phenyl or phenyl substituted with at least one group selected from Substituent group α, and particularly preferably phenyl.

Substituent group a preferably consists of $C_1$-$C_4$ alkyl groups, $C_1$-$C_4$ alkoxy groups and $C_1$-$C_4$ alkylthio groups, and more preferably it consists of methyl, ethyl, methoxy and methylthio.

$G^1$ is preferably a $C_1$-$C_4$ linear or branched alkylene group, more preferably a $C_1$-$C_3$ linear alkylene group, even more preferably methylene or ethylene, and most preferably methylene.

$R^1$ is preferably a $C_3$-$C_6$ branched alkyl group; an aralkyl group comprising from 1 to 3 $C_6$-$C_{10}$ aryl groups and a $C_1$-$C_3$ alkyl group; or a $C_7$-$C_{15}$ aralkyl group in which the aryl ring is substituted with a $C_1$-$C_4$ alkyl or $C_1$-$C_4$ alkoxy group, more preferably tert-butyl, 1,1-dimethylpropyl, 1,1,2-trimethylpropyl, benzyl, diphenylmethyl, triphenylmethyl, 4-methylbenzyl or 4-methoxybenzyl, and particularly preferably tert-butyl, 1,1-dimethylpropyl or triphenylmethyl.

$R^2$ is preferably a hydrogen atom; a $C_1$-$C_4$ alkanoyl group; trifluoroacetyl; methoxyacetyl; benzoyl; 1-naphthoyl; 2-naphthoyl; anisoyl; nitrobenzoyl; a $C_1$-$C_4$ alkoxycarbonyl group; 2,2,2-trichloroethoxycarbonyl; triethylsilylmethoxycarbonyl; 2-(trimethylsilyl)ethoxycarbonyl; vinyloxycarbonyl; allyloxycarbonyl; a $C_1$-$C_6$ linear or branched alkyl group; a $C_3$-$C_6$ linear or branched 2-alkenyl group; an aralkyl group comprising from 1 to 3 $C_6$-$C_{10}$ aryl groups and a $C_1$-$C_3$ alkyl group; benzyloxycarbonyl; or nitrobenzyloxycarbonyl; more preferably a hydrogen atom, formyl, acetyl, benzoyl, p-anisoyl, 4-nitrobenzoyl, methoxycarbonyl, ethoxycarbonyl, butoxycarbonyl, tert-butoxycarbonyl, methyl, ethyl, tert-butyl, 1,1-dimethylbutyl, 1,1-dimethylpropyl, 1,1,2-trimethylpropyl, allyl, 1-methyl-2-propenyl, benzyl, 1-phenylethyl, benzyloxycarbonyl or 4-nitrobenzyloxycarbonyl, and particularly preferably a hydrogen atom, methoxycarbonyl, ethoxycarbonyl, tert-butoxycarbonyl, tert-butyl, 1,1-dimethylbutyl, 1,1-dimethylpropyl or 1-phenylethyl.

$R^5$ is preferably a phenyl group substituted with from 1 to 3 groups selected from the group consisting of hydroxyl groups, methoxy, ethoxy, trifluoromethyl, trichloromethyl, difluoromethyl, fluoromethyl and tetrazolyl, more preferably a phenyl group substituted with from 1 to 3 groups selected from the group consisting of hydroxyl groups, methoxy, trifluoromethyl and tetrazolyl (examples of which include a 3,5-bis(trifluoromethyl)phenyl, 3,4,5-trimethoxyphenyl, 3-hydroxy-4,5-dimethoxyphenyl, 4-hydroxy-3,5-dimethoxyphenyl or 2-methoxy-5-(1-tetrazolyl)phenyl), even more preferably a phenyl group substituted with from 1 to 3 groups selected from the group consisting of methoxy, trifluoromethyl and tetrazolyl (examples of which include a 3,5-bis(trifluoromethyl)phenyl, 3,4,5-trimethoxyphenyl or 2-methoxy-5-(1-tetrazolyl)phenyl), and particularly preferably a 3,5-bis(trifluoromethyl)phenyl or 3,4,5-trimethoxyphenyl.

$R^6$ is preferably a phenyl group substituted with 1 or 2 fluorine atoms or chlorine atoms, more preferably a phenyl group substituted with two fluorine atoms or chlorine atoms, even more preferably 3,4-difluorophenyl or 3,4-dichlorophenyl, and particularly preferably 3,4-dichlorophenyl.

$X^1$ and $X^2$ are the same or different and each preferably is a chlorine atom or bromine atom, and particularly preferably a bromine atom.

n is preferably 2.

In addition, a preferred compound among the compounds represented by the aforementioned general formula (5) is a compound selected from the following:

tert-butyl 4-{2-[(tert-butylthio)methyl]phenyl}4-hydroxypiperidine-1-carboxylate, ethyl 4-{2-[(tert-butylthio)methyl]phenyl}-4-hydroxypiperidine-1-carboxylate, methyl 4-{2-[(tert-butylthio)methyl]phenyl}-4-hydroxypiperidine-1-carboxylate, benzyl 4-{2-[(tert-butylthio)methyl]phenyl}-4-hydroxypiperidine-1-carboxylate,
tert-butyl 4-(2-{[(1,1-dimethylpropyl)thio]methyl}phenyl)-4-hydroxypiperidine-1-carboxylate,
ethyl 4-(2-{[(1,1-dimethylpropyl)thio]methyl}phenyl)-4-hydroxypiperidine-1-carboxylate,
methyl 4-(2-{[(1,1-dimethylpropyl)thio]methyl}phenyl)-4-hydroxypiperidine 1-carboxylate,
benzyl 4-(2-{[(1,1-dimethylpropyl)thio]methyl}phenyl)-4-hydroxypiperidine-1-carboxylate,
1-allyl-4-{2-[(tert-butylthio)methyl]phenyl}piperidin-4-ol,
1-tert-butyl 4-{2-[(tert-butylthio)methyl]phenyl}piperidin-4-ol,
4-{2-[(tert-butylthio)methyl]phenyl}-1-(1,1-dimethylpropyl)piperidin-4-ol,
4-{2-[(tert-butylthio)methyl]phenyl}-1-ethylpiperidin-4-ol,
4-{2-[(tert-butylthio)methyl]phenyl}-1-methylpiperidin-4-ol,
1-benzyl-4-{2-[(tert-butylthio)methyl]phenyl}piperidin-4-ol,
4-{2-[(tert-butylthio)methyl]phenyl}-1-(1-phenylethyl)piperidin-4-ol,
1-allyl-4-(2-{[(1,1-dimethylpropyl)thio]methyl}phenyl)piperidin-4-ol,
1-tert-butyl-4-(2-{[(1,1-dimethylpropyl)thio]methyl}phenyl)piperidin-4-ol,
1-(1,1-dimethylpropyl)-4-(2-{[(1,1-dimethylpropyl)thio]methyl}phenyl)piperidin-4-ol,
4-(2-{[(1,1-dimethylpropyl)thio]methyl}phenyl)-1-ethylpiperidin-4-ol,
4-(2-{[(1,1-dimethylpropyl)thio]methyl}phenyl)-1-methylpiperidin-4-ol,
1-benzyl 4-(2-{[(1,1-dimethylpropyl)thio]methyl}phenyl)piperidin-4-ol,
4-(2-{[(1,1-dimethylpropyl)thio]methyl}phenyl)-1-(1-phenylethyl)piperidin-4-ol,
1-acetyl-4-{2-[(tert-butylthio)methyl]phenyl}piperidin-4-ol,
1-acetyl-4-(2-{[(1,1-dimethylpropyl)thio]methyl}phenyl)piperidin-4-ol,
4-{2-[(tert-butylthio)methyl]phenyl}piperidin-4-ol, and
4-(2-{[(1,1-dimethylpropyl)thio]methyl}phenyl)piperidin-4-ol.

The process for producing cyclic thioethers of the present invention is carried out in accordance with the first, second and third steps indicated below:

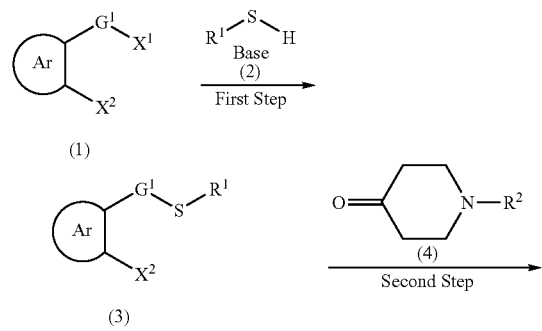

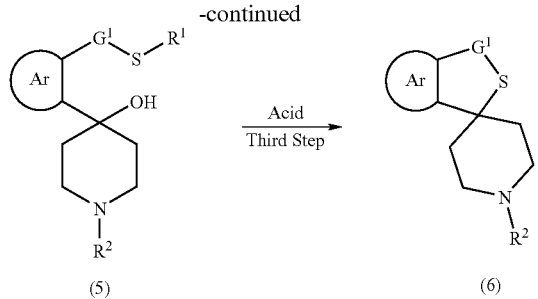

(wherein, Ar, $G^1$, $R^1$, $R^2$, $X^1$ and $X^2$ have the same meanings as defined above).

The first step is a step, wherein a compound (3) is produced by reacting a halogenated aryl compound (1) with a thiol compound (2) in an inert solvent in the presence of a base.

There is no particular limitation on the inert solvent to be used, provided that it does not impair the reaction and that it dissolves the starting substance, and it can be, for example, an aliphatic hydrocarbon such as hexane, heptane or petroleum ether; an aromatic hydrocarbon such as benzene, toluene or xylene; an ether such as diethyl ether, diisopropyl ether, dibutyl ether, tert-butyl methyl ether, tetrahydrofuran or dioxane; a halogenated hydrocarbon such as methylene chloride, chloroform, carbon tetrachloride or dichloroethane; an amide such as N,N-dimethylformamide or N,N-dimethylacetamide; an alcohol such as methanol, ethanol, propyl alcohol, isopropyl alcohol, butyl alcohol or tert-butyl alcohol; a nitrile such as acetonitrile; water; or mixtures of water and the aforementioned "aliphatic hydrocarbons", "aromatic hydrocarbons", "ethers", "halogenated hydrocarbons", "amides", "alcohols" or "nitriles", preferably an alcohol; water; or a mixture of water and an alcohol, and more preferably methanol, ethanol, isopropyl alcohol, water or a mixture thereof.

The base to be used can be, for example, an alkaline metal hydroxide such as lithium hydroxide, sodium hydroxide or potassium hydroxide; an alkaline metal carbonate such as sodium carbonate, potassium carbonate, sodium hydrogencarbonate or potassium hydrogencarbonate; an alkaline metal hydride such as lithium hydride, sodium hydride or potassium hydride; an alkaline metal phosphate such as potassium phosphate or sodium phosphate; an alkaline metal alkoxide such as lithium methoxide, sodium tert-butoxide, lithium ethoxide, sodium methoxide, sodium ethoxide or potassium tert-butoxide; or an organic amine such as trimethylamine, triethylamine, diisopropylamine, N,N-diisopropylethylamine, imidazole, N-methylimidazole, N-methylmorpholine, 1,8-diazabicyclo[5.4.0]undec-7-ene (DBU), 1,5-diazabicyclo[4.3.0]non-5-ene (DBN), 1,4-diazabicyclo[2.2.2]octane (DABCO), pyridine, 4-dimethylaminopyridine, picoline, N,N-dimethylaniline or N-methylpyrrolidine, preferably an alkaline metal hydroxide, and particularly preferably sodium hydroxide. These salts may also be added to the reaction in the form of an aqueous solution if desired.

The amount of the base to be used is preferably 0.5 to 10 equivalents (more preferably 0.8 to 2 equivalents) relative to 1 equivalent of the aforementioned halogenated aryl compound (1).

The amount of the aforementioned thiol compound (2) to be used is preferably 0.5 to 5 equivalents (more preferably 0.8 to 1.5 equivalents) relative to 1 equivalent of the aforementioned halogenated aryl compound (1).

The reaction temperature is normally −80 to 100° C. (preferably −20 to 50° C.), and while the reaction time varies depending on the reaction temperature and so forth, it is normally 10 minutes to 20 hours (preferably 0.5 hour to 4 hours).

After the reaction, the desired compound is recovered from the reaction mixture in accordance with ordinary methods.

For example, after suitably neutralizing the reaction mixture and removing any insoluble matter by filtration if present, water is added followed by extracting with an immiscible organic solvent like toluene, washing with water and so forth, drying the extract with anhydrous magnesium sulfate and so forth and distilling off the solvent to obtain the desired compound.

The resulting compound can be separated and purified by ordinary methods such as silica gel chromatography as necessary.

The second step is a step wherein a compound (3) is reacted with an organometallic reagent or metal in an inert solvent to produce a carbanion, after which the reaction mixture is reacted with a ketone compound (4) to produce compound (5).

There is no particular limitation on the inert solvent to be used, provided that it does not impair the reaction and that it dissolves the starting substance, it can be, for example, an aliphatic hydrocarbon such as hexane, heptane or petroleum ether; an aromatic hydrocarbon such as benzene, toluene or xylene; an ether such as diethyl ether, diisopropyl ether, dibutyl ether, tert-butyl methyl ether, 1,2-dimethoxyethane, diglyme, tetrahydrofuran or dioxane; an amide such as N,N-dimethylformamide or N,N-dimethylacetamide; or a mixture thereof, preferably an aliphatic hydrocarbon, an aromatic hydrocarbon, an ether or a mixture thereof, and more preferably hexane, diethyl ether, tetrahydrofuran, toluene or a mixture thereof.

The organometallic reagent to be used to form the carbanion can be, for example, organolithium reagent such as methyl lithium, butyl lithium, sec-butyl lithium, tert-butyl lithium, hexyl lithium, phenyl lithium, lithium diisopropylamide and lithium bis(trimethylsilyl)amide; or a Grignard's reagent such as methyl magnesium-chloride, methyl magnesium bromide, isopropyl magnesium chloride and butyl magnesium chloride, preferably an organolithium reagent, and more preferably butyl lithium or hexyl lithium. The amount of the organometallic reagent to be used is preferably 0.5 to 10 equivalents (more preferably 0.8 to 1.5 equivalents and particularly preferably 0.9 to 1.1 equivalents) relative to 1 equivalent of compound (3).

The metals to be used to form the carbanion can be, for example, lithium (Li), sodium (Na), potassium (K), magnesium (Mg), copper (Cu) or zinc (Zn), and preferably lithium or magnesium. The amount of metal to be used is preferably 0.5 to 10 equivalents (more preferably 0.8 to 2.2 equivalents and particularly preferably 0.9 to 2 equivalents) with respect to 1 equivalent of compound (3).

In the case of reacting compound (3) with an organometallic reagent, the reaction temperature is preferably −100 to 100° C. (more preferably −80 to −20° C.), and while the reaction time varies depending on temperature and so forth, it is normally 1 minute to 20 hours, and preferably 5 minutes to 3 hours.

In the case of allowing a metal to act on compound (3), the reaction temperature is preferably −80 to 100° C. (more preferably −10 to 80° C.), and while the reaction time varies depending on the temperature and so forth, it is normally 10 minutes to 20 hours, and preferably 1 hour to 4 hours.

The amount of the aforementioned ketone compound (4) to be used is preferably 0.5 to 10 equivalents (more preferably 0.8 to 1.5 equivalents) with respect to 1 equivalent of compound (3).

The reaction temperature in the case of adding the aforementioned ketone compound (4) to the carbanion of the compound (3) during the latter stage of the reaction is preferably −100 to 100° C. (more preferably −80 to −20° C.), and while the reaction time varies depending on the reaction temperature and so forth, it is normally 10 minutes to 10 hours and preferably 0.5 hours to 2 hours.

After the reaction, the desired compound is recovered from the reaction mixture in accordance with ordinary methods.

For example, after suitably neutralizing the reaction mixture and removing any insoluble matter by filtration if present, water is added followed by extracting with an immiscible organic solvent like toluene, washing with water and so forth, drying the extract with anhydrous magnesium sulfate and so forth and distilling off the solvent to obtain the desired compound.

The resulting compound can be separated and purified by ordinary methods such as recrystallization, reprecipitation or silica gel chromatography as necessary.

The third step is a step wherein the thiol protecting group of compound (5) is removed in the presence of an acid followed by a dehydration reaction to produce a cyclic thioether compound (6).

The acid to be used can be, for example, an inorganic acid such as hydrogen chloride, hydrochloric acid, phosphoric acid, hydrogen bromide, hydrobromic acid, hydrogen iodide, hydroiodic acid or sulfuric acid; an organic acid such as acetic acid, trifluoroacetic acid, p-toluenesulfonic acid or methanesulfonic acid; or a mixture of these inorganic acids and organic acids, with preferred examples of inorganic acids that are used being hydrogen chloride, hydrochloric acid, hydrogen bromide, hydrobromic acid or sulfuric acid, and preferred examples of organic acids that are used being trifluoroacetic acid, p-toluenesulfonic acid or methanesulfonic acid (more preferably trifluoroacetic acid). In addition, in the case of using a mixture of an inorganic acid and organic acid, acetic acid is also used preferably as an organic acid.

In the case of using an inorganic acid, the amount of acid to be used is 3 to 50 equivalents (preferably 5 to 30 equivalents) relative to 1 equivalent of compound (5). In the case of using an organic acid, the amount of acid to be used is 3 to 50 equivalents (preferably 5 to 20 equivalents) with respect to 1 equivalent of compound (5). In the case of using a mixture of an inorganic acid and organic acid, although there are no particular limitations on their ratio, they are preferably used by combining 3 to 50 equivalents (preferably 5 to 30 equivalents) of inorganic acid with 3 to 50 equivalents (preferably 5 to 20 equivalents) of organic acid relative to 1 equivalent of compound (5).

The reaction temperature is normally 0 to 150° C. (preferably 80 to 120° C.), and while the reaction time varies depending on the reaction temperature and so forth, it is normally 10 minutes to 20 hours and preferably 5 hours to 20 hours.

Furthermore, there are also cases in which the amino protecting group is also removed at the stage of removing the thiol protecting group ($R^1$) in this step. In such cases, after the aforementioned dehydration reaction, protection is performed in compliance with established methods as desired, and the reaction can be carried out in accordance with, for example, the following methods 1 to 3.

<Method 1>

Method 1 is a method to carry out protection by reacting 0.5 to 4 equivalents (preferably 0.8 to 2 equivalents) of a compound having the general formula: $R^3$—$Y'$ or a compound having the general formula: $R^4$—O—$R^4$ [wherein $R^3$ represents a "an amino protecting group" as in the definition of $R^2$, $R^4$ represents the aforementioned "$C_1$-$C_6$ alkanoyl group", "$C_1$-$C_4$ alkanoyl group substituted with halogen or $C_1$-$C_4$ alkoxy", "unsaturated $C_2$-$C_4$ alkanoyl group", "$C_6$-$C_{10}$ arylcarbonyl group which may be substituted with halogen, $C_1$-$C_4$ alkyl, $C_1$-$C_4$ alkoxy, $C_1$-$C_4$ alkoxycarbonyl, $C_6$-$C_{10}$ aryl or nitro", "$C_1$-$C_4$ alkoxycarbonyl group which may be substituted with halogen or $C_1$-$C_4$ alkylsilyl", "$C_2$-$C_5$ alkenyloxycarbonyl group", "$C_7$-$C_{15}$ aralkyloxycarbonyl group which may be substituted with methoxy or nitro", "lower alkanesulfonyl group such as methanesulfonyl or ethanesulfonyl" or "halogeno lower alkanesulfonyl group such as a trifluoromethanesulfonyl or pentafluoroethanesulfonyl", which were aforementioned as the "amino protecting group", and although $Y'$ represents a leaving group, there are no particular limitations on said leaving group, provided that it is a leaving group normally used during nucleophilic substitution reactions, and preferably a halogen atom such as chlorine, bromine or iodine; lower alkoxycarbonyloxy group such as methoxycarbonyloxy or ethoxycarbonyloxy; halogenated alkylcarbonyloxy group such as chloroacetyloxy, dichloroacetyloxy, trichloroacetyloxy or trifluoroacetyloxy; lower alkanesulfonyloxy group such as methanesulfonyloxy or ethanesulfonyloxy; halogeno lower alkanesulfonyloxy group such as trifluoromethanesulfonyloxy or pentafluoroethanesulfonyloxy; or arylsulfonyloxy group such as benzenesulfonyloxy, p-tolueneulfonyloxy or 4-nitrobenzenesulfonyloxy, and more preferably a halogen atom, a halogeno lower alkanesulfonyloxy group or arylsulfonyloxy group, and even more preferably a chlorine atom or bromine atom] with the resulting product (de-protected product) in an inert solvent in presence or absence of a base.

There is no particular limitation on the inert solvent to be used, provided that it does not impair the reaction and that it dissolves the starting substance to a certain degree, it is preferably an aliphatic hydrocarbon such as hexane or heptane, an aromatic hydrocarbon such as benzene, toluene or xylene, a halogenated hydrocarbon such as methylene chloride, chloroform, carbon tetrachloride, dichloroethane, chlorobenzene or dichlorobenzene, an ester such as ethyl formate, ethyl acetate, propyl acetate, butyl acetate or diethyl carbonate, an ether such as diethyl ether, diisopropyl ether, tetrahydrofuran, dioxane, dimethoxyethane or diethylene glycol dimethyl ether, a nitrile such as acetonitrile or isobutyronitrile, and an amide such as formamide, N,N-dimethylformamide, N,N-dimethylacetamide, N-methyl-2-pyrrolidone, N-methylpyrrolidinone or hexamethylphosphorotriamide; water, and a mixture of water and the aforementioned organic solvents.

There is no particular limitation on the base to be used, provided that it is used as a base in ordinary reactions, and it is preferably an alkaline metal hydroxide such as lithium hydroxide, sodium hydroxide or potassium hydroxide; an alkaline metal carbonate such as sodium carbonate, potassium carbonate, sodium hydrogencarbonate or potassium hydrogencarbonate; an alkaline metal phosphate such as potassium phosphate or sodium phosphate; and an organic amine such as N-methylmorpholine, triethylamine, tributylamine, N,N-diisopropylethylamine, dicyclohexylamine, N-methylpiperidine, pyridine, 4-pyrrolidinopyridine, picoline, 4-dimethylaminopyridine, 2,6-di(tert-butyl)-4-methylpyridine, quinoline, N,N-dimethylaniline or N,N-diethylaniline.

Furthermore, 4-dimethylaminopyridine and 4-pyrrolidinopyridine can also be used in catalytic amounts in combination with other bases, and quaternary ammonium salts such as benzyltriethylammonium chloride or tetrabutylammonium chloride, or crown ethers such as dibenzo-18-crown-6 can also be added in order to carry out the reaction effectively.

The reaction temperature is normally from −20° C. to the reflux temperature of the solvent to be used, and preferably from 0° C. to room temperature.

While the reaction time varies depending mainly on the reaction temperature, raw material compounds, type of base used and type of solvent to be used, it is normally from 10 minutes to 3 days, preferably from 1 hour to 1 day.

Specific examples of compounds having the general formula $R^3$—$Y'$ include aliphatic acyl halides such as acetyl chloride, propionyl chloride, butyryl bromide, valeryl chloride or hexanoyl chloride; acyl halides like lower alkoxycarbonyl halides such as methoxycarbonyl chloride, methoxycarbonyl bromide, ethoxycarbonyl chloride, propoxycarbonyl chloride, butoxycarbonyl chloride or hexyloxycarbonyl chloride, or arylcarbonyl halides such as benzoyl chloride, benzoyl bromide or naphthoyl chloride; silyl halides such as tert-butyldimethylsilyl chloride, trimethylsilyl chloride, triethylsilyl chloride, triethylsilyl bromide, triisopropylsilyl chloride, isopropyldimethylsilyl chloride, diethylisopropylsilyl chloride, tert-butyldiphenylsilyl chloride, methyldiphenylsilyl chloride or triphenylsilyl chloride; silyl trifluoromethanesulfonates corresponding to the silyl halides; aralkyl halides such as benzyl chloride or benzyl bromide; lower alkanesulfonyl halides such as methanesulfonyl chloride; or arylsulfonyl halides such as p-toluenesulfonyl chloride or 4-nitrobenzenesulfonyl chloride.

Compounds having the general formula: $R^4$—O—$R^4$ may be, for example, aliphatic carboxylic anhydrides such as acetic anhydride, propionic anhydride, valeric anhydride or hexanoic anhydride; halogeno lower alkanesulfonic anhydrides such as trifluoromethanesulfonic anhydride; or mixed acid anhydrides like those of formic acid and acetic acid.

<Method 2>

Method 2 is a method to carry out protection by reacting a compound having the general formula: $R^4$—OH (wherein $R^4$ is the same as previously defined) with the resulting product (de-protected product) in an inert solvent in the presence of a condensing agent and in the presence or absence of base.

There is no particular limitation on the inert solvent to be used, provided that it does not impair the reaction and that it dissolves the starting substance to a certain degree, preferred examples of which include aliphatic hydrocarbons such as hexane or heptane; aromatic hydrocarbons such as benzene, toluene or xylene; halogenated hydrocarbons such as methylene chloride, chloroform, carbon tetrachloride, dichloroethane, chlorobenzene or dichlorobenzene; esters such as ethyl formate, ethyl acetate, propyl acetate, butyl acetate or diethyl carbonate; ethers such as diethyl ether, diisopropyl ether, tetrahydrofuran, dioxane, dimethoxyethane or diethylene glycol dimethyl ether; nitriles such as acetonitrile or isobutyronitrile; or amides such as formamide, N,N-dimethyl formamide, N,N-dimethylacetamide. N-methyl-2-pyrrolidone, N-methylpyrrolidinone or hexamethylphosphortriamide.

As to the base to be used, the same bases as those described in the aforementioned <Method 1> can be used.

Examples of condensing agents used include:

(1) combinations of phosphate esters such as diethylphosphoryl cyanide or diphenylphosphoryl azide and the aforementioned bases;

(2) carbodiimides such as 1,3-dicyclohexylcarbodiimide, 1,3-diisopropylcarbodiimide or 1-ethyl-3-(3-dimethylaminopropyl)carbodiimide; combinations of the aforementioned bases and the aforementioned carbodiimides; or, combinations of the aforementioned carbodiimides and N-hydroxy compounds such as N-hydroxysuccinimide, 1-hydroxybenzotriazole or N-hydroxy-5-norbornene-2,3-dicarboximide;

(3) combinations of disulfides such as 2,2'-dipyridyl disulfide or 2,2'-dibenzothiazolyl disulfide and phosphines such as triphenylphosphine or tributylphosphine;

(4) carbonates such as N,N'-disuccinimidylcarbonate, di-2-pyridylcarbonate or S,S'-bis(1-phenyl-1H-tetrazol-5-yl)dithiocarbonate;

(5) phosphinic chlorides such as N,N'-bis(2-oxo-3-oxazolidinyl)phosphinic chloride;

(6) oxalates such as N,N'-disuccinimidyloxalate, N,N'-diphthalimideoxalate, N,N'-bis(5-norbornene-2,3-dicarboximidyl)oxalate, 1,1'-bis(benzotriazolyl)oxalate, 1,1'-bis(6-chlorobenzotriazolyl)oxalate or 1,1'-bis(6-trifluoromethylbenzotriazolyl)oxalate;

(7) combinations of the aforementioned phosphines and azodicarboxylic esters or azodicarboxylic amides such as diethyl azodicarboxylate or 1,1'-(azodicarbonyl)dipiperidine; or, combinations of the aforementioned phosphines and the aforementioned bases;

(8) N-lower alkyl-5-arylisoxazolium-3'-sulfonates such as N-ethyl-5-phenylisoxazolium-3'-sulfonate;

(9) diheteroaryl diselenides such as di-2-pyridyldiselenide;

(10) arylsulfonyltriazolides such as 4-nitrobenzenesulfonyl triazolide;

(11) 2-halo-1-lower alkylpyridinium halides such as 2-chloro-1-methylpyridinium iodide;

(12) imidazoles such as 1,1'-oxazolyldiimidazole or N,N'-carbonyldiimidazole;

(13) 3-lower alkyl-2-halogen-benzothiazolium fluoroborates such as 3-ethyl-2-chloro-benzothiazolium fluoroborate;

(14) 3-lower alkyl-benzothiazole-2-selones such as 3-methyl-benzothiazole-2-selone;

(15) phosphates such as phenyldichlorophosphate and polyphosphate ester;

(16) halogenosulfonylisocyanates such as chlorosulfonyl isocyanate;

(17) halogenosilanes such as trimethylsilyl chloride or triethylsilyl chloride;

(18) combinations of lower alkanesulfonyl halides such as methanesulfonyl chloride and the aforementioned bases; and,

(19) N,N,N',N'-tetra lower alkyl halogenoformamidium chlorides such as N,N,N',N'-tetramethylchloroformamidium chloride, while preferred examples are those indicated in (1) above.

The reaction temperature is normally −20 to 80° C. and preferably 0° C. to room temperature.

While the reaction time varies depending mainly on the reaction temperature, raw material compounds, reaction reagents or type of solvent used, it is normally from 10 minutes to 3 days and preferably from 30 minutes to 1 day.

<Method 3>

In the case that the amino protecting group is a tert-butoxycarbonyl or benzyloxycarbonyl, the nitrogen atom can be protected by reacting a tert-butoxycarbonylation agent or benzyloxycarbonylation agent with the resulting compound (de-protected product) in an inert solvent and in the presence or absence of base.

The inert solvent used is the same inert solvent as described in the aforementioned <Method 1>.

The base used is the same base as described in the aforementioned <Method 1>.

The tert-butoxycarbonylation agent used is preferably di-tert-butyl dicarbonate, 2-(tert-butoxycarbonyloximino)-2-phenylacetonitrile, tert-butyl S-(4,6-dimethylpyrimidin-2-yl)thiolcarboxylate or 1,2,2,2-tetrachloroethyl tert-butylcarbonate, and more preferably di-tert-butyl dicarbonate.

The benzyloxycarbonylation agent used is preferably benzyloxycarbonyl chloride, benzyloxycarbonyl cyanide or dibenzyl dicarbonate.

The reaction temperature is normally −20 to 80° C. and preferably 0° C. to room temperature.

While the reaction time varies depending mainly on the reaction temperature, raw material compound, reaction reagents or types of solvents used, it is normally from 10 minutes to 3 days and preferably from 30 minutes to 1 day.

After the reaction, the desired compound is recovered from the reaction mixture in accordance with ordinary methods.

For example, after suitably neutralizing the reaction mixture and removing any insoluble matter by filtration if present, water is added followed by extracting with an immiscible organic solvent like toluene, washing with water and so forth, drying the extract with anhydrous magnesium sulfate and so forth and distilling off the solvent to obtain the desired compound.

The resulting compound can be separated and purified by ordinary methods such as recrystallization, reprecipitation or silica gel chromatography as necessary.

Since the aforementioned cyclic thioether compound (6) can be easily transformed to a neurokinin receptor antagonist according to the method disclosed in, for example, WO 95/28389 and U.S. Pat. No. 6,159,967, it is useful as a raw material compound for pharmaceuticals. More specifically, a neurokinin receptor antagonist can be produced by carrying out a reaction according to the fourth and fifth steps described below.

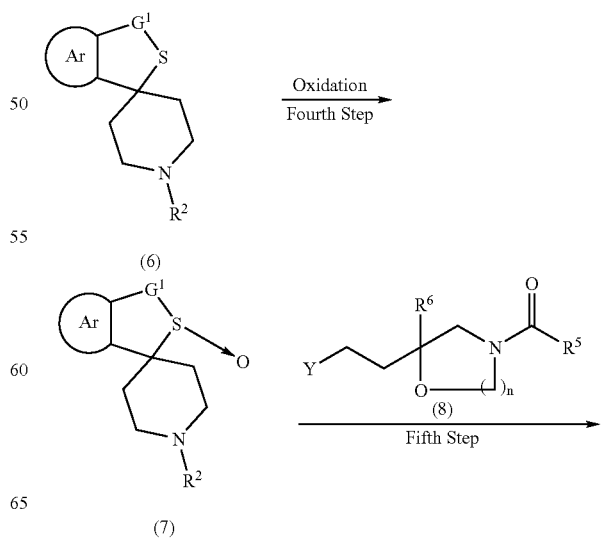

-continued

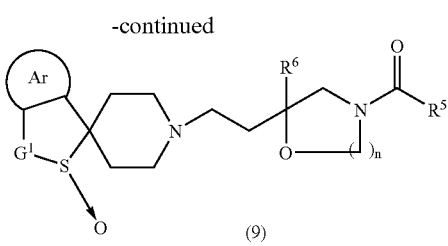

(9)

(wherein Ar, G$^1$, R$^2$, R$^5$, R$^6$, Y and n have the same meanings as defined above).

The fourth step is a step wherein an oxidizing agent is allowed to react with cyclic thioether compound (6) in an inert solvent to produce cyclic sulfoxide compound (7).

There is no particular limitation on the inert solvent to be used, provided that it does not impair the reaction and that it dissolves the starting substance to a certain degree, preferred examples of which include organic solvents including aliphatic hydrocarbons such as hexane or heptane, aromatic hydrocarbons such as benzene, toluene or xylene, lower alcohols such as methanol, ethanol, propanol, isopropanol, butanol, sec-butanol or tert-butanol, ketones such as acetone, ethyl methyl ketone or isopropyl methyl ketone, halogenated hydrocarbons such as methylene chloride, chloroform, carbon tetrachloride, dichloroethane, chlorobenzene or dichlorobenzene, lower alkanoic acids such as formic acid, acetic acid or propionic acid, esters such as ethyl formate, ethyl acetate, propyl acetate, butyl acetate or diethyl carbonate, ethers such as diethyl ether, diisopropyl ether, tetrahydrofuran, dioxane, dimethoxyethane or diethylene glycol dimethyl ether, nitriles such as acetonitrile or isobutyronitrile, and amides such as formamide, N,N-dimethylformamide, N,N-dimethylacetamide, N-methyl-2-pyrrolidone, N-methylpyrrolidinone or hexamethylphosphortriamide; water; and mixtures of water and the aforementioned organic solvents, and more preferably aromatic hydrocarbons, halogenated hydrocarbons, lower alkanoic acids, ketones or mixtures of water and these organic solvents.

There is no particular limitation on the oxidizing agent to be used, provided that it oxidizes sulfides to form sulfoxides, examples of which include inorganic peroxides such as hydrogen peroxide, sodium periodate or potassium peroxodisulfate; and organic peroxides such as dimethyldioxirane, ethylmethyldioxirane, isopropylmethyldioxirane, performic acid, peracetic acid, pertrifluoroacetic acid, perbenzoic acid, m-chloroperbenzoic acid, magnesium monoperoxyphthalate, tert-butyl hydroperoxide or cumene hydroperoxide, preferably peroxides such as hydrogen peroxide, peracetic acid, dimethyldioxirane, ethylmethyldioxirane, isopropylmethyldioxirane, tert-butyl hydroperoxide or cumene hydroperoxide, and more preferably hydrogen peroxide or dimethyldioxirane. Furthermore, in the case of using dimethyldioxirane, ethylmethyldioxirane or isopropylmethyldioxirane as the oxidizing agent, adjustments can be made within the reaction system using the corresponding ketone and potassium peroxymonosulfate (KHSO$_5$).

Moreover, in the case water or a water-containing solvent is used as the inert solvent, an inorganic halogen compound such as a chlorine molecule, bromine molecule, sulfuryl chloride or sodium hypochlorite; or, an organic halogen compound such as N-bromosuccinimide, N-chlorosuccinimide, chloramine-T or tert-butyl hypochloride can be used.

The amount of the oxidizing agent used is preferably 0.1 to 20 equivalents (and more preferably 0.5 to 1.5 equivalents) with respect to 1 equivalent of cyclic thioether compound (6).

The reaction temperature is normally −20 to 100° C. (and preferably 0 to 10° C.), and while the reaction time varies depending on the reaction temperature and so forth, it is normally from 10 minutes to 20 hours and preferably from 1 hour to 6 hours.

Furthermore, in the case where an optically active cyclic sulfoxide compound (7) is desired in the present step, either (a) optical resolution is carried out on a racemic cyclic sulfoxide compound (7), or (b) an optically active form is obtained by asymmetric oxidation of compound (6) directly.

(a-1) In the case of carrying out optical resolution by diastereomeric salt formation, after removal of the amino protecting group from the racemic cyclic sulfoxide compound (7) if it is present, a salt is formed using a suitable optically active carboxylic acid for the optical resolution reagent followed by separation crystallization to obtain an optically active salt of cyclic sulfoxide compound (7).

Removal of the amino protecting group in the first stage of the reaction can be carried out in accordance with known methods, and can be removed by, for example, treating with acid or base in an inert solvent.

There is no particular limitation on the solvent to be used, provided that it does not impair the reaction and that it dissolves the starting substance to a certain degree, examples of which include aliphatic hydrocarbons such as hexane, heptane, ligroin or petroleum ether; aromatic hydrocarbons such as benzene, toluene or xylene; halogenated hydrocarbons such as dichloromethane, chloroform, carbon tetrachloride, dichloroethane, chlorobenzene, o-dichlorobenzene, m-dichlorobenzene, fluorobenzene, trichloromethylbenzene or trifluoromethylbenzene; ethers such as diethyl ether, diisopropyl ether, tetrahydrofuran, dioxane, dimethoxyethane or diethyleneglycol dimethyl ether; esters such as methyl acetate or ethyl acetate; alcohols such as methanol, ethanol, propanol, 2-propanol or butanol; amides such as formamide. N,N-dimethylformamide, N,N-dimethylacetamide or hexamethylphosphorotriamide; sulfoxides such as dimethyl sulfoxide or sulfolane; fatty acids such as formic acid or acetic acid; or water or mixtures of water and the aforementioned solvents, preferably halogenated hydrocarbons, ethers, alcohols, fatty acids or mixtures of water and the aforementioned solvents, and more preferably halogenated hydrocarbons (particularly chlorobenzene, o-dichlorobenzene, m-dichlorobenzene or trifluoromethylbenzene), ethers (particularly tetrahydrofuran or dioxane), fatty acids (particularly acetic acid), alcohols (particularly methanol or ethanol) or mixtures of water and the aforementioned solvents.

The acid used is, for example, hydrogen chloride, hydrochloric acid, sulfuric acid, phosphoric acid, hydrogen bromide, hydrobromic acid or trifluoroacetic acid, and preferably hydrochloric acid, sulfuric acid, hydrobromic acid or trifluoroacetic acid.

Examples of the base to be used include alkaline metal carbonates such as sodium carbonate, potassium carbonate or lithium carbonate; alkaline metal hydrogencarbonates such as sodium hydrogencarbonate, potassium hydrogencarbonate or lithium hydrogencarbonate; alkaline metal hydrides such as lithium hydride, sodium hydride or potassium hydride; alkaline metal hydroxides such as sodium hydroxide, potassium hydroxide or lithium hydroxide; alkaline metal alkoxides such as sodium methoxide, sodium ethoxide, potassium tert-butoxide or lithium methoxide; alkaline metal mercaptans such as sodium methylmercaptan or sodium ethylmercaptan; or organic bases such as hydrazine, methylamine, dimethylamine, ethylamine, triethylamine, tributylamine, diisopropylethylamine, N-methylmorpholine, pyridine, 4-dimethylaminopyridine, N,N-dimethylaniline, N,N-diethylaniline, 1,5-diazabicyclo[4.3.0]non-5-ene, 1,4-diazabicyclo[2.2.2]octane (DABCO) or 1,8-diazabicyclo[5.4.0]undec-7-ene (DBU), and preferably alkaline metal carbonates (particularly sodium carbonate or potassium carbonate), alkaline metal hydroxides (particularly sodium hydroxide or potassium hydroxide), alkaline metal alkoxides (particularly sodium methoxide, sodium ethoxide or potassium-tert-butoxide) or organic bases (particularly hydrazine or methyl amine).

While the reaction temperature varies depending on the raw material compound, solvent or acid or base used, it is normally −10 to 150° C. and preferably 0 to 100° C.

While the reaction time varies depending on the raw material compound, solvent or acid or base used, it is normally from 5 minutes to 48 hours and preferably from 10 minutes to 15 hours.

The optical resolution reagent to be used for carrying out optical resolution is, for example, tartaric acid, camphor-10-sulfonic acid or mandelic acid, and preferably mandelic acid.

Although there are no particular limitations on the solvent used, it is preferably acetonitrile.

An optically active form of cyclic sulfoxide compound (7) can be obtained by converting the obtained salt into the free form by using an aqueous alkaline solution such as sodium hydroxide and then by extracting with a solvent that does not dissolve in water (examples of which include aromatic hydrocarbons such as benzene, toluene or xylene; halogenated hydrocarbons such as methylene chloride or chloroform; ethers such as ether, tetrahydrofuran, dioxane or dimethoxyethane, alcohols such as butanol, sec-butanol or tert-butanol; or nitriles such as acetonitrile, propionitrile or isobutyronitrile).

(a-2) In addition, an optically active form of cyclic sulfoxide compound (7) can be obtained by applying a racemic cyclic sulfoxide compound (7) to chromatography using a column packed with silica gel for optical resolution.

(b) Optically active oxidizing agents, chemical techniques combining an optically active ligand and oxidizing agent, and biological techniques using bread yeast or other microbes are known regarding asymmetric oxidation for obtaining sulfoxides from sulfides. Examples of this asymmetric oxidation are described in the following documents.

1) G. Solladie, Synthesis 185 (1981):

2) K. K. Andersen, The Chemistry of Sulfones and Sulfoxides: S. Patai, Z. Rappoport, C. J. M. Stirling., Eds. Wiley & Sons, Ltd.; Chichester, England, 1988, Chapter 3, pp 55-94: G. H. Posner., ibid. Chapter 16, pp 823-849:

3) H. B. Kagan et al., Synlett 643 (1990):

4) H. B. Kagan, "Asymmetric Oxidation of Sulfides" in "Catalytic Asymmetric Synthesis" 1, Ojima Ed. VCH, pp 203-226 (1993):

5) F. A. Davis et al., J. Am. Chem. Soc., 114, 1428 (1992))□

Among these, the asymmetric oxidation using (3'S,2R)-(−)-N-(phenylsulfonyl)(3,3-dichlorocamphoryl)oxaziridine or (+)-[8,8-dimethoxycamphoryl)sulfonyl]oxaziridine reported by F. A. Davis et al. is particularly preferable.

In the case of carrying out asymmetric oxidation according to the method of F. A. Davis et al., the inert solvent used is preferably an aliphatic hydrocarbon such as hexane or heptane; an aromatic hydrocarbon such as benzene, toluene or xylene; a halogenated hydrocarbon such as methylene chloride, chloroform, carbon tetrachloride, dichloroethane, chlorobenzene or dichlorobenzene; an ester such as ethyl formate, propyl acetate, butyl acetate or diethyl carbonate; an ether such as diethyl ether, diisopropyl ether, tetrahydrofuran, dioxane, dimethoxyethane or diethylene glycol dimethyl ether; a nitrile such as acetonitrile or isobutyronitrile; or pyridine.

The reaction temperature, for example, can be −50 to 50° C. and is preferably −20° C. to room temperature.

While reaction time varies depending mainly on the reaction temperature, raw material compound, reaction reagents and solvent used, it is normally from 10 minutes to 3 days and preferably from 2 hours to 1 day.

The fifth step is a step, wherein the compound (9) is produced by removing the amino protecting group from the cyclic sulfoxide compound (7) if present, and reacting the resulting compound with compound (8).

Removal of the amino protecting group ($R^2$) is carried out according to the procedure for removal of the amino protecting group of the fourth step.

The reaction between the compound obtained in the first stage reaction and compound (8) is carried out in an inert solvent and in the presence of base.

There is no particular limitation on the inert solvent to be used, provided that it does not impair the reaction and that it dissolves the starting substance to a certain degree, examples of which include aliphatic hydrocarbons such as hexane, heptane, ligroin or petroleum ether; aromatic hydrocarbons such as benzene, toluene or xylene; halogenated hydrocarbons such as methylene chloride, chloroform, carbon tetrachloride, dichloroethane, chlorobenzene or dichlorobenzene; esters such as ethyl formate, ethyl acetate, propyl acetate, butyl acetate or diethyl carbonate; ethers such as diethyl ether, diisopropyl ether, tetrahydrofuran, dioxane, dimethoxyethane or diethyleneglycol dimethyl ether; ketones such as acetone, ethyl methyl ketone, isobutyl methyl ketone, isophorone or cyclohexanone; nitro compounds such as nitroethane or nitrobenzene; nitriles such as acetonitrile or isobutyronitrile; amides such as formamide, N,N-dimethylformamide, N,N-dimethylacetamide, N-methyl-2-pyrrolidone, N-methylpyrrolidinone or hexamethylphosphorotriamide; or sulfoxides such as dimethyl sulfoxide or sulfolane, preferably amides, ethers or nitriles, and particularly preferably nitriles.

There is no particular limitation on the base to be used, provided that it is used as a base in ordinary reactions, examples of which include inorganic bases including alkaline metal carbonates such as sodium carbonate, potassium carbonate or lithium carbonate; alkaline earth metal carbonates such as calcium carbonate or barium carbonate; alkaline metal hydrogencarbonates such as sodium hydrogencarbonate, potassium hydrogencarbonate or lithium hydrogencarbonate; alkaline metal hydrides such as lithium hydride, sodium hydride or potassium hydride; alkaline metal hydroxides such as sodium hydroxide, potassium hydroxide or lithium hydroxide; or, alkaline earth metal hydroxides such as calcium hydroxide or barium hydroxide; or, organic bases such as N-methylmorpholine, triethylamine, tripropylamine, tributylamine, N,N-diisopropylethylamine, dicyclohexylamine, N-methylpiperidine, pyridine, 4-pyrrolidinopyridine, picoline, 4-dimethylaminopyridine, 2,6-di(tert-butyl)$_4$-methylpyridine, quinoline, N,N-dimethylaniline, N,N-diethylaniline, 1,5-diazabicyclo[4.3.0]non-5-ene (DBN), 1,4-diazabicyclo[2.2.2]octane (DABCO) or 1,8-diazabicyclo[5.4.0]undec-7-ene (DBU), preferably inorganic bases, and most preferably alkaline metal hydrogencarbonates. Furthermore, the addition of a catalytic amount of an alkaline metal iodide such as potassium iodide or sodium iodide is useful for the purpose of accelerating the reaction.

The reaction temperature can be, for example, 0 to 150° C., and preferably 20 to 120° C.

While the reaction time varies depending mainly on the reaction temperature, raw material compound, reaction reagents or inert solvent used, it is usually from 30 minutes to 48 hours and preferably from 1 hour to 12 hours.

After the reaction, the desired compound is recovered from the reaction mixture in accordance with ordinary methods.

For example, after adding water to the reaction mixture and extracting with an immiscible solvent such as toluene, the extract is washed with water and so forth and then dried with anhydrous magnesium sulfate, etc. to obtain the desired compound after distilling off the solvent.

The resulting compound can be separated and purified by ordinary methods such as re-crystallization, re-precipitation or silica gel chromatography if necessary.

Moreover, compound (9) can be easily derivatised to a pharmaceutically acceptable salt by treating in accordance with ordinary methods using an acid (examples of which include an inorganic acid such as hydrogen chloride, sulfuric acid or phosphoric acid, or an organic acid such as acetic acid, fumaric acid or succinic acid, and preferably hydrogen chloride or fumaric acid) if desired.

The following provides a more detailed description of the present invention through its examples and reference examples, but the present invention is not limited thereto.

EXAMPLES

Example 1 tert-Butyl spiro[benzo[c]thiophene-1(3H),4'-piperidine]-1'-carboxylate (a) 1-bromo-2-[(tert-butylthio)methyl]benzene

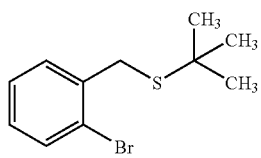

36.6 g (406 mmol) of tert-butylmercaptan were added to a mixed solution of 36.5 g (438 mmol) of 48% aqueous sodium hydroxide solution and 400 ml of methanol under a nitrogen atmosphere at room temperature. A solution of 99.5 g (398 mmol) of 2-bromobenzylbromide in 100 ml of methanol were dropped into this solution below 40° C. After stirring for 30 minutes at 40° C. 1000 ml of toluene and 500 ml of water were sequentially added to the reaction solution. The aqueous layer was separated, and the organic layer was sequentially washed with 500 ml of 5% aqueous sodium hydroxide solution and 500 ml of water. After drying the organic layer with magnesium sulfate, the solvent was distilled off to obtain 300 ml of residue, which was used in the next step.

$^1$H-NMR (400 MHz, CDCl$_3$) δ ppm: 1.39 (s, 9H), 3.89 (s, 2H), 7.08(dt, J=7.6 and 1.5 Hz, 1H), 7.25 (t, J=7.6 Hz, 1H), 7.44 (dd, J=7.8 and 1.5 Hz, 1H), 7.53 (d, J=7.8 Hz, 1H).

(b) Ethyl 4-{2-[(tert-butylthio)methyl]phenyl}-4-hydroxypiperidine-1-carboxylate

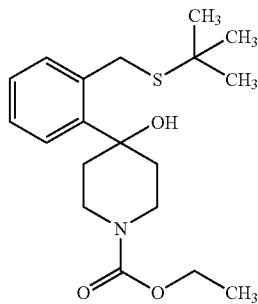

After 253.3 ml (398 mmol) of butyl lithium-hexane solution were dropped into 500 ml of tetrahydrofuran cooled below –70° C. under a nitrogen atmosphere, a toluene solution of the 1-bromo-2-[(tert-butylthio)methyl]benzene (398 mmol), obtained in Example 1(a), was dropped in over the course of one hour while maintaining at –70° C. After stirring for 15 minutes at the same temperature, a solution of 74.9 g (438 mmol) of N-ethoxycarbonyl-4-piperidone in 300 ml of toluene was dropped in over the course of 1 hour or more while maintaining at –70° C. After stirring for 1 hour at the same temperature, the temperature was raised to about –20° C. followed by the sequential addition of 500 ml of 20% aqueous ammonium chloride solution and 350 ml of toluene. The aqueous layer was separated, and the organic layer was washed with 500 ml of 20% aqueous sodium chloride solution. After concentrating the organic layer under reduced pressure, 200 ml of toluene and 1000 ml of heptane were added to the residue followed by stirring for 1 hour at room temperature. After cooling to 0 to 5° C. and stirring for an additional 30 minutes, the precipitated crystals were filtered out. The resulting crystals were dried for 15 hours under reduced pressure at 50° C. to obtain 101 g of crude ethyl 4-{2-[(tert-butylthio)methyl]phenyl}-4-hydroxypiperidine-1-carboxylate as white crystals (crude yield: 72.2%, purity: 96.4%).

$^1$H-NMR (400 MHz, CDCl$_3$) δ ppm: 1.28 (t, J=7.1 Hz, 3H), 1.41 (s, 9H), 1.87-2.07 (m, 4H), 3.22 (s, 1H), 3.25-3.45 (m, 2H), 3.95-4.25 (m, 2H), 4.16 (s, 2H), 4.16 (q, J=7.1 Hz, 2H), 7.17-7.30 (m, 4H).

$^{13}$C-NMR (100 MHz, CDCl$_3$) δ ppm: 14.59, 30.56, 32.36, 38.30, 39.67, 43.33, 61.03, 72.90, 126.07, 127.09, 127.24, 133.43, 134.79, 145.20, 155.45.

FAB-MS m/z: 352 [(M+H)$^+$];

Anal. Calcd for C$_{19}$H$_{29}$NO$_3$S: C, 64.92; H, 8.32; N, 3.98; S, 9.12. Found: C, 64.90; H, 8.34. N, 3.98 S, 9.10.

(c) Tert-Butyl spiro[benzo[c]thiophene-1(3H),4'-piperidine]-1'-carboxylate 100 g (274 mmol) of the crude ethyl 4-{2-[(tert-butylthio) methyl]phenyl}-4-hydroxypiperidine-1-carboxylate, obtained in Example 1(c), were added to a mixed solution of 200 ml (1.77 mmol) of 48% hydrobromic acid and 300 mol (5.24 mmol) of acetic acid under a nitrogen atmosphere followed by heating under reflux condition for 6 hours. After concentrating the reaction mixture under reduced pressure to 250 ml of residue, 100 ml of water and 500 ml of toluene were sequentially added. A 25% aqueous sodium hydroxide solution was dropped in until the pH reached 13 to 14 followed by stirring for 30 minutes after heating to 40° C. After cooling to 10° C. or lower, 62.8 g (288 mmol) of di-tert-butyldicarbonate were dropped in followed by stirring for 1 hour at room temperature. After stirring for an additional 30 minutes at 35 to 40° C., 500 ml of toluene were added followed by separation of the aqueous layer. After washing the organic layer twice with 500 ml of 10% aqueous sodium chloride solution, it was concentrated under reduced pressure. After adding 200 ml of methanol to the residue and stirring for 30 minutes under reflux conditions, the solution was additionally stirred for 30 minutes at room temperature. After cooling to 0 to 5° C. and additionally stirring for 30 minutes, the precipitated crystals were filtered out. The resulting crystals were then dried for 15 hours at 50° C. under reduced pressure to obtain 79.5 g of tert-butyl spiro[benzo[c]thiophene-1(3H),4'-piperidine]-1'-carboxylate as pale yellow crystals (crude yield: 91.5%, purity: 99.2%).

$^1$H-NMR (400 MHz, CDCl$_3$) δ ppm: 1.48 (s, 9H), 1.80-1.92 (m, 2H), 2.05 (dt, J=13.0 and 4.4 Hz, 2H), 2.80-3.13 (m, 2H), 4.05-4.35 (m, 2H), 4.18 (s, 2H), 7.14-7.27 (m, 4H).

Example 2

4-{2-[(tert-Butylthio)methyl]phenyl}-1-ethylpiperidin-4-ol

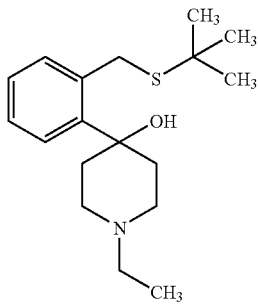

After 12.1 ml (19.0 mmol) of a solution of butyl lithium in hexane were dropped into 25 ml of tetrahydrofuran cooled below −70° C. under nitrogen atmosphere, a toluene solution of the 1-bromo-2-[(tert-butylthio)methyl]benzene (19.0 mmol), obtained in Example 1(a), was dropped in over the course of 1 hour or more while maintaining at −70° C. After stirring for 5 minutes at the same temperature, a solution of 2.66 g (20.9 mmol) of 1-ethyl-4-piperidone in 15 ml of toluene was dropped in over the course of 30 minutes while maintaining at −70° C. After stirring for 1 hour at the same temperature, the temperature was raised to about −20° C. followed by the addition of 25 ml of 20% aqueous ammonium chloride solution. The aqueous layer was separated, and the organic layer was washed with 25 ml of 20% aqueous sodium chloride solution. After concentrating the organic layer under reduced pressure, 5 ml of toluene and 30 ml of hexane were added to the residue followed by stirring for 1 hour with ice-cooling and filtering out the precipitated crystals. The resulting crystals were then dried for 15 hours at 40° C. under reduced pressure to obtain 2.85 g of 4-{2-[(tert-butylthio) methyl]phenyl}-1-ethylpiperidin-4-ol as white crystals (crude yield: 48.8%).

$^1$H-NMR (400 MHz, CDCl$_3$) δ ppm: 1.13 (t, J=7.1 Hz, 3H), 1.41 (s, 9H), 1.90-2.10 (m, 2H), 2.18 (dt, J=12.9 and 4.4 Hz, 2H), 2.47-2.54 (m, 2H), 2.50 (q, J=7.1 Hz, 2H), 2.78-2.87 (m, 2H), 2.93 (s, 1H), 4.19 (s, 2H), 7.15-7.38 (m, 4H).

$^{13}$C-NMR (100 MHz, CDCl$_3$) δ ppm: 11.64, 30.36, 31.65, 37.99, 42.69, 48.41, 51.87, 72.01, 125.57, 126.48, 126.63, 132.91, 135.18, 145.57.

FAB-MS m/z: 308 [(M+H)$^+$].

Example 3

1-Benzyl-4-{2-[(tert-butylthio)methyl] phenyl}piperidin-4-ol

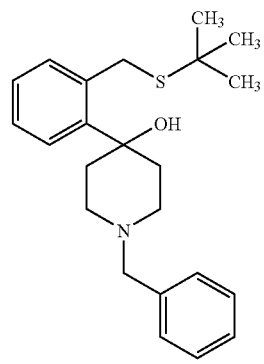

After 12.1 ml (19.0 mmol) of a solution of butyl lithium in hexane were dropped into 25 ml of tetrahydrofuran cooled below −70° C. under nitrogen atmosphere, a toluene solution of the 1-bromo-2-[(tert-butylthio)methyl]benzene (19.0 mmol), obtained in Example 1(a), was dropped in over the course of 1 hour or more while maintaining at −70° C. After stirring for 5 minutes at the same temperature, a solution of 4.00 g (20.9 mmol) of 1-benzyl-4-piperidone in 15 ml of toluene was dropped in over the course of 30 minutes while maintaining at −70° C. After stirring for 1 hour at the same temperature, the temperature was raised to about −20° C. followed by the addition of 25 ml of 20% aqueous ammonium chloride solution. The aqueous layer was separated, and the organic layer was washed with 25 ml of 20% aqueous sodium chloride solution. After concentrating the organic layer under reduced pressure, it was purified by silica gel column chromatography to obtain 4.52 g of 1-benzyl-4-{2-[(tert-butylthio)methyl]phenyl}piperidin-4-ol as an oily substance (yield: 64.4%). $^1$H-NMR (400 MHz, CDCl$_3$) δ ppm: 1.41 (s, 9H), 1.88-1.98 (m, 2H), 2.19 (dt, J=12.9 and 4.4 Hz, 2H), 2.57 (dt, J=12.0 and 2.2 Hz, 2H), 2.70-2.80 (m, 2H), 2.82 (s, 1H), 3.58 (s, 2H), 4.17 (s, 2H), 7.15-7.35 (m, 9H).

$^{13}$C-NMR (100 MHz, CDCl$_3$) δ ppm: 30.54, 32.04, 38.44, 42.99, 49.10, 63.00, 72.57, 125.94, 126.66, 126.77, 126.89, 127.92, 128.92, 133.15, 135.03, 138.51, 145.67.

FAB-MS m/z: 370 [(M+H)$^+$].

REFERENCE EXAMPLES

Reference Example 1 tert-Butyl spiro[benzo[c]thiophene-1(3H),4'-piperidine]-1'-carboxylate 2-oxide 10.0 g of the crude tert-butyl spiro[benzo[c]thiophene-1(3H),4'-piperidine]-1'-carboxylate, obtained in Example 1, were added to 50 ml of methylene chloride and 150 ml of acetone followed by cooling to 0 to 5° C. A solution of 15.0 g (24.4 mmol) of Oxone™ in 75 ml of water was dropped in at 5° C. or lower followed by stirring for 3 hours at 0 to 5° C. A solution of 1.72 g (9.8 mmol) of sodium thiosulfate-hydrate in 50 ml of water was added followed by stirring for 30 minutes at 20 to 25° C. 100 ml of methylene chloride and 100 ml of water were then added followed by separation of the aqueous layer. After washing the organic layer with 100 ml of water, it was dried with anhydrous magnesium sulfate followed by distilling off the solvent to obtain 10.5 g of tert-butyl spiro[benzo[c]thiophene-1-(3H),4'-piperidine]-1'-carboxylate 2-oxide as a white foamy substance (crude yield: 100%).

$^1$H-NMR (400 MHz, CDCl$_3$) δ ppm: 1.50 (s, 9H), 1.60-1.66 (m, 1H), 1.86-1.94 (m, 1H), 2.16-2.24 (m, 1H), 2.40-2.48 (m, 1H), 3.10-3.30 (m, 2H), 4.05 (d, J=16.8 Hz, 1H), 4.10-4.30 (m, 2H), 4.37 (d, J=16.8 Hz, 1H), 7.20-7.40 (m, 4H).

Reference Example 2

1-{2-[(2R)-(3,4-Dichlorophenyl)-4-[3,5-bis(trifluoromethyl)benzoyl]morpholin-2-yl]ethyl}spiro[benzo[c]thiophene-1(3H),4'-piperidine]-(2S)-oxide hydrochloride (a) 2-{(2R)-(3,4-dichlorophenyl)-4-[3,5-bis(trifluoromethyl)benzoyl]morpholin-2-yl}ethyl methanesulfonate 5.60 g (20.3 mmol) of 2-[(2R)-(3,4-dichlorophenyl)morpholin-2-yl]ethanol (U.S. Pat. No. 6,159,967, Example 51(d)) were dissolved in methylene chloride (60 ml) followed by the addition of 2.83 ml (24.3 mmol) of triethylamine. 5.60 g (20.3 mmol) of 3,5-bis(trifluoromethyl)benzoyl chloride and 248 mg (2.03 mmol) of 4-dimethylaminopyridine were added with ice-cooling followed by stirring for 2 hours at room temperature under a nitrogen atmosphere. Water was then added to the reaction solution followed by washing the methylene chloride layer with water and a saturated aqueous solution of sodium chloride, and drying with anhydrous magnesium sulfate. After filtering, the solvent was distilled off under reduced pressure and the residue was purified by silica gel column chromatography (elution solvent: hexane/ethyl acetate=1/1) to obtain 5.68 g of 2-{(2R)-(3,4-dichlorophenyl)-4-[3,5-bis(trifluoromethyl)benzoyl]morpholin-2-yl}ethanol (54%).

5.68 g (11 mmol) of the resulting alcohol derivative were dissolved in methylene chloride (60 ml) followed by the addition of 2.3 ml (16.5 mmol) of triethylamine under a nitrogen atmosphere, the addition of 1.02 ml (13.2 mmol) of methanesulfonyl chloride with ice-cooling, and stirring for 30 minutes at room temperature under a nitrogen atmosphere. Water was then added to the reaction solution followed by washing the methylene chloride layer with water and a saturated aqueous solution of sodium chloride and drying with anhydrous magnesium sulfate. After filtering, the solvent was distilled off under reduced pressure and the residue was purified by silica gel column chromatography (elution solvent: hexane/ethyl acetate=3/2) to obtain 6.09 g of the desired compound (93%).

$^1$H-NMR (400 MHz, CDCl$_3$) δ ppm: 2.16-2.52 (m, 2H), 2.95 (s, 3H), 3.23-4.08 (m, 6H), 4.19-4.56 (m, 2H), 7.29-7.70 (m, 3H), 7.71-8.05 (m, 3H).

FAB-MS m/z: 594 [(M+H)$^+$].

(b) 1-{2-[(2R)-(3,4-dichlorophenyl)-4-[3,5-bis(trifluoromethyl)benzoyl]morpholin-2-yl]ethyl}spiro[benzo[c]thiophene-1(3H),4'-piperidine]-(2S)-oxide Hydrochloride 400 mg (0.67 mmol) of the 2-{(2R)-(3,4-dichlorophenyl)-4-[3,5-bis(trifluoromethyl)benzoyl]morpholin-2-yl}ethyl methanesulfonate, obtained in Reference Example 2(a), were dissolved in 4 ml of dimethylacetamide followed by the addition of 170 mg (2.02 mmol) of sodium hydrogencarbonate, 168 mg (1.01 mmol) of potassium iodide and 191 mg (0.74 mmol) of spiro[c]thiophene-[(3H),4'-piperidine]-(2S)-oxide hydrochloride (U.S. Pat. No. 6,159,967, Preparation 6) and stirring for 8 hours at 80° C. Water was then added to the reaction solution followed by extracting twice with ethyl acetate, combining the ethyl acetate layers, washing with water and a saturated aqueous solution of sodium chloride and drying with anhydrous magnesium sulfate. After filtering, the solvent was distilled off under reduced pressure and the residue was purified by silica gel column chromatography (elution solvent: methylene chloride/methanol=50/1) to obtain 408 mg of 1-{2-[(2R)-(3,4-dichlorophenyl)-4-[3,5-bis(trifluoromethyl)benzoyl]morpholin-2-yl]ethyl}spiro{benzo[c]thiophene-1(3H),4'-piperidine]-(2S)-oxide (84%).

408 mg (0.57 mmol) of the resulting free form were dissolved in 8 ml of ethanol followed by the addition of 0.71 ml (2.84 mmol) of 4N solution of hydrochloric acid in dioxane with ice-cooling under nitrogen atmosphere. After stirring for 10 minutes with ice-cooling, the solvent was distilled off under reduced pressure and azeotropic drying with diethyl ether. The resulting residue was crystallized from diethyl ether to obtain 363 mg of the desired compound as white crystals (85%).

$^1$H-NMR (500 MHz, CD$_3$OD) δ ppm: 2.03-2.12 (m, 1H), 2.27-2.42 (m, 2H), 2.47-2.57 (m, 1H), 2.67-2.81 (m, 2H), 2.91-3.10 (m, 1H), 3.16-3.35 (m, 3H), 3.38-4.11 (m, 8H), 4.15 (d, J=17.2 Hz, 1H), 4.86 (d, J=17.2 Hz, 1H), 7.36-7.47 (m, 4H), 7.48-8.18 (m, 6H).

FAB-MS m/z: 719 [(M+H)$^+$, free form].

Cyclic thioether compounds are used as, for example, starting raw materials of neurokinin receptor antagonists (WO 95/28389 and U.S. Pat. No. 6,159,967), and in the process of the present invention, cyclic thioether compounds can be produced in fewer steps, less expensively and at higher yield as compared with known processes.

The invention claimed is:

1. A process for producing a compound having the following formula (6):

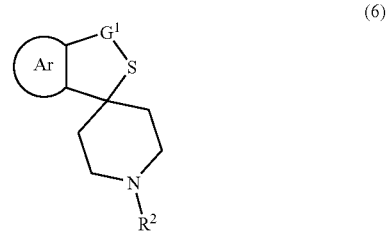

(6)

wherein $R^2$ represents a hydrogen atom or an amino protecting group, $G^1$ represents a $C_1$-$C_6$ alkylene group and Ar represents an unsubstituted phenyl group or a phenyl group substituted with at least one group from Substituent group α;

Substituent group α is selected from the group consisting of a $C_1$-$C_6$ alkyl group, a $C_1$-$C_6$ alkoxy group and a $C_1$-$C_6$ alkylthio group, comprising reacting a compound having the formula (1):

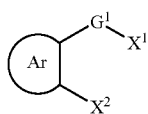

(1)

wherein $X^1$ and $X^2$ are the same or different and each represents a halogen atom, and $G^1$ and Ar have the same meanings as defined above, with a compound having the formula (2):

(2)

wherein $R^1$ represents a thiol protecting group, to produce a compound represented by the formula (3):

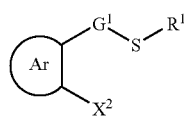

(3)

wherein $R^1$, $G^1$, $X^2$ and Ar have the same meanings as defined above, and after reacting the compound of formula (3) with a metal or organometallic reagent that forms a carbanion of the compound of formula (3), reacting a compound having the formula (4):

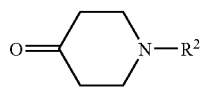

(4)

wherein $R^2$ has the same meaning as defined above, with the resulting reaction mixture to produce a compound having the formula (5):

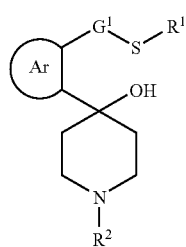

(5)

wherein $R^1$, $R^2$, $G^1$ and Ar have the same meanings as defined above, carrying out a dehydration reaction after removal of the group $R^1$ of the compound having the formula (5), and optionally protecting the nitrogen atom with an amino protecting group.

2. The process according to claim 1, wherein $G^1$ represents a $C_1$-$C_4$ linear or branched alkylene group.

3. The process according to claim 1, wherein $R^1$ represents a $C_3$-$C_6$ branched alkyl group; an aralkyl group comprising from 1 to 3 $C_6$-$C_{10}$ aryl groups and a $C_1$-$C_3$ alkyl group; or a $C_7$-$C_{15}$ aralkyl group in which the aryl ring thereof is substituted with a $C_1$-$C_4$ alkyl group or $C_1$-$C_4$ alkoxy group.

4. The process according to claim 1, wherein $R^2$ represents a hydrogen atom; a $C_1$-$C_4$ alkanoyl group; trifluoroacetyl; methoxyacetyl; benzoyl; 1-naphthoyl; 2-naphthoyl; anisoyl; nitrobenzoyl; a $C_1$-$C_4$ alkoxycarbonyl group; 2,2,2-trichloroethoxycarbonyl; triethylsilylmethoxycarbonyl; 2-(trimethylsilyl)ethoxycarbonyl; vinyloxycarbonyl; allyloxycarbonyl; a $C_1$-$C_6$ linear or branched alkyl group; a $C_3$-$C_6$ linear or branched 2-alkenyl group; an aralkyl group comprising from 1 to 3 $C_6$-$C_{10}$ aryl groups and a $C_1$-$C_3$ alkyl group; benzyloxycarbonyl; or nit robenzyloxycarbonyl.

5. The process according to claim 1, wherein $X^1$ and $X^2$ are the same or different and each represents a chlorine atom or bromine atom.

6. The process according to claim 1, wherein $G^1$ represents a $C_1$-$C_4$ linear or branched alkylene group;

$R^1$ represents a $C_3$-$C_6$ branched alkyl group; an aralkyl group comprising from 1 to 3 $C_6$-$C_{10}$ aryl groups and a $C_1$-$C_3$ alkyl group; or a $C_7$-$C_{15}$ aralkyl group in which the aryl ring thereof is substituted with a $C_1$-$C_4$ alkyl group or $C_1$-$C_4$ alkoxy group;

$R^2$ represents a hydrogen atom; a $C_1$-$C_4$ alkanoyl group; trifluoroacetyl; methoxyacetyl; benzoyl; 1-naphthoyl; 2-naphthoyl; anisoyl; nitrobenzoyl; a $C_1$-$C_4$ alkoxycarbonyl group; 2,2,2-trichloroethoxycarbonyl; triethylsilylmethoxycarbonyl ; 2-(trimethylsilyl)ethoxycarbonyl; vinyloxycarbonyl; allyloxycarbonyl; a $C_1$-$C_6$ linear or branched alkyl group; a $C_3$-$C_6$ linear or branched 2-alkenyl group; an aralkyl group comprising from 1 to 3 $C_6$-$C_{10}$ aryl groups and a $C_1$-$C_3$ alkyl group; benzyloxycarbonyl; or nitrobenzyloxycarbonyl; and $X^1$ and $X^2$ are the same or different and each represents a chlorine atom or bromine atom.

7. A process for producing a compound having the formula (6):

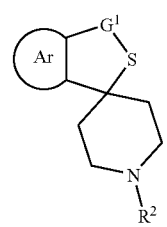

(6)

wherein $R^2$ represents a hydrogen atom or an amino protecting group, $G^1$ represents a $C_1$-$C_6$ alkylene group, and Ar represents an unsubstituted phenyl group or a phenyl group substituted with at least one group from Substituent group α;

Substituent group α is selected from the group consisting of a $C_1$-$C_6$ alkyl group, a $C_1$-$C_6$ alkoxy group and a $C_1$-$C_6$ alkylthio group, comprising carrying out a dehydration reaction after removing a group $R^1$ from a compound represented by formula (5):

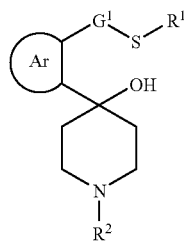

(5)

wherein $R^1$ represents a thiol protecting group, and $R^2$, $G^1$ and Ar have the same meanings as defined above, and then optionally protecting the nitrogen atom with an amino protecting group.

8. The process according to claim 7, wherein $G^1$ represents a $C_1$-$C_4$ linear or branched alkylene group.

9. The process according to claim 7, wherein $R^1$ represents a $C_3$-$C_6$ branched alkyl group; an aralkyl group comprising from 1 to 3 $C_6$-$C_{10}$ aryl groups and a $C_1$-$C_3$ alkyl group; or a $C_7$-$C_{15}$ aralkyl group in which the aryl ring thereof is substituted with a $C_1$-$C_4$ alkyl group or $C_1$-$C_4$ alkoxy group.

10. The process according to claim 7, wherein $R^2$ represents a hydrogen atom; a $C_1$-$C_4$ alkanoyl group; trifluoroacetyl; methoxyacetyl; benzoyl; 1-naphthoyl; 2-naphthoyl; anisoyl; nitrobenzoyl; a $C_1$-$C_4$ alkoxycarbonyl group; 2,2,2-trichloroethoxycarbonyl; triethylsilylmethoxycarbonyl; 2-(trimethylsilyl)ethoxycarbonyl; vinyloxycarbonyl; allyloxycarbonyl; a $C_1$-$C_6$ linear or branched alkyl group; a $C_3$-$C_6$ linear or branched 2-alkenyl group; an aralkyl group comprising from 1 to 3 $C_6$-$C_{10}$ aryl groups and a $C_1$-$C_3$ alkyl group; benzyloxycarbonyl; or nitrobenzyloxycarbonyl.

11. The process according to claim 7, wherein $G^1$ represents a $C_1$-$C_4$ linear or branched alkylene group;

$R^1$ represents a $C_3$-$C_6$ branched alkyl group; an aralkyl group comprising from 1 to 3 $C_6$-$C_{10}$ aryl groups and a $C_1$-$C_3$ alkyl group; or a $C_7$-$C_{15}$ aralkyl group in which the aryl ring thereof is substituted with a $C_1$-$C_4$ alkyl group or $C_1$-$C_4$ alkoxy group; and $R^2$ represents a hydrogen atom; a $C_1$-$C_4$ alkanoyl group; trifluoroacetyl; methoxyacetyl; benzoyl; 1-naphthoyl; 2-naphthoyl; anisoyl; nitrobenzoyl; a $C_1$-$C_4$ alkoxycarbonyl group; 2,2,2-trichloroethoxycarbonyl; triethylsilylmethoxycarbonyl; 2-(trimethylsilyl)ethoxycarbonyl; vinyloxycarbonyl; allyloxycarbonyl; a $C_1$-$C_6$ linear or branched alkyl group; a $C_3$-$C_6$ linear or branched 2-alkenyl group; an aralkyl group comprising from 1 to 3 $C_6$-$C_{10}$ aryl groups and a $C_1$-$C_3$ alkyl group; benzyloxycarbonyl; or nitrobenzyloxycarbonyl.

* * * * *